US011589597B2

(12) United States Patent
Segall et al.

(10) Patent No.: US 11,589,597 B2
(45) Date of Patent: Feb. 28, 2023

(54) PREPARATION OF PULSE PROTEIN PRODUCTS (YP810)

(71) Applicant: Burcon NutraScience (MB) Corp., Winnipeg (CA)

(72) Inventors: Kevin I. Segall, Winnipeg (CA); Brent E. Green, Warren (CA); Martin Schweizer, Winnipeg (CA)

(73) Assignee: Burcon Nutrascience (MB) Corp.

( * ) Notice: Subject to any disclaimer, the term of this patent is extended or adjusted under 35 U.S.C. 154(b) by 345 days.

(21) Appl. No.: 14/811,052

(22) Filed: Jul. 28, 2015

(65) Prior Publication Data
US 2016/0050956 A1 Feb. 25, 2016

Related U.S. Application Data

(60) Provisional application No. 62/029,686, filed on Jul. 28, 2014.

(51) Int. Cl.
| A23J 1/14 | (2006.01) |
| C07K 14/415 | (2006.01) |
| C07K 1/34 | (2006.01) |
| A23L 2/66 | (2006.01) |
| A23J 3/14 | (2006.01) |
| A23J 3/16 | (2006.01) |

(52) U.S. Cl.
CPC ............. *A23J 1/14* (2013.01); *A23J 3/14* (2013.01); *A23J 3/16* (2013.01); *A23L 2/66* (2013.01); *C07K 1/34* (2013.01); *C07K 14/415* (2013.01)

(58) Field of Classification Search
None
See application file for complete search history.

(56) References Cited

U.S. PATENT DOCUMENTS

| 3,966,702 | A | 6/1976 | Carey |
| 4,169,090 | A | 9/1979 | Murray et al. |
| 4,208,323 | A | 6/1980 | Murray et al. |
| 4,296,026 | A | 10/1981 | Millar |
| 4,307,014 | A | 12/1981 | Millar |
| 4,366,097 | A | 12/1982 | Cameron et al. |
| 4,418,013 | A | 11/1983 | Cameron et al. |
| 4,677,065 | A | 6/1987 | Buchbjerg et al. |
| 5,520,935 | A | 5/1996 | Eriksen et al. |
| 5,844,086 | A | 12/1998 | Murray |
| 6,005,076 | A | 12/1999 | Murray |
| 7,090,887 | B2 | 8/2006 | Newkirk et al. |
| 10,506,821 | B2 | 12/2019 | Segall et al. |
| 2005/0123649 | A1 | 6/2005 | Benitez et al. |
| 2005/0165220 | A1 | 7/2005 | Barker et al. |
| 2005/0255226 | A1 | 11/2005 | Schweizer et al. |
| 2007/0014909 | A1 | 1/2007 | Mai et al. |
| 2007/0065567 | A1 | 3/2007 | Segall et al. |
| 2008/0226810 | A1 | 9/2008 | Passe et al. |
| 2008/0280024 | A1 | 11/2008 | Harle et al. |
| 2010/0098818 | A1 | 4/2010 | Schweizer et al. |
| 2010/0203203 | A1* | 8/2010 | Segall ............. A23L 2/66 426/330 |
| 2011/0038993 | A1 | 2/2011 | Schweizer et al. |
| 2011/0274797 | A1 | 11/2011 | Segall et al. |
| 2012/0135117 | A1 | 5/2012 | Segall et al. |
| 2013/0129901 | A1 | 5/2013 | Segall et al. |
| 2013/0189408 | A1 | 7/2013 | Segall et al. |
| 2014/0017379 | A1 | 1/2014 | Segall et al. |
| 2014/0256914 | A1 | 9/2014 | Green et al. |

FOREIGN PATENT DOCUMENTS

| WO | 2005107492 A1 | 11/2005 |
| WO | 2010045727 A1 | 4/2010 |
| WO | 2010083612 A1 | 7/2010 |

OTHER PUBLICATIONS

Sumner et al. ,"Production and Evaluation of Pea Protein Isolate"—J. Food Science, vol. 46, pp. 364-372 (1981). (Year: 1981).*
Swanson, B. "Pea and Lentil Protein Extraction and Functionality", JAOCS, vol. 67. No. 5, (1990), pp. 276-280. (Year: 1990).*
Naczk et al.,"Functional Properties and Phytate Content of Pea Protein Preparations", Journal of Food Science, vol. 51, No. 5, (1986), pp. 1245-1247. (Year: 1986).*
Sumner et al.,"Production and Evaluation of Pea Protein Isolate", Journal of Food Science, vol. 46, (1981), pp. 364-372. (Year: 1981).*
Vose, J.R., "Production and functionality of Starches and Protein Isolates from Legume Seeds (Field Peas and Horsebeans)", Cereal Chemistry, 57 (6), 1980, pp. 406-410. (Year: 1980).*

(Continued)

*Primary Examiner* — Elizabeth Gwartney

(57) ABSTRACT

The present invention is directed to pulse protein products, very low in, or substantially free of, pea/vegetable flavour notes characteristic of conventional commercial pulse protein products and useful for the fortification of food and beverage products and prepared without the use of salt in the process. The pulse protein products of the present invention are obtained by extracting pulse protein source with water to form an aqueous pulse protein solution, at least partially separating the aqueous pulse protein solution from residual pulse protein source, adjusting the pH of the aqueous pulse protein solution to a pH of about 1.5 to about 3.4 to solubilize the bulk of the protein and form an acidified pulse protein solution then separating the acidified pulse protein solution from the acid insoluble solid material. The acidified pulse protein solution may be dried following optional concentration and diafiltration to form a pulse protein product, which may be an isolate. The acid insoluble solid material may be washed with acidified water and then dried to form another pulse protein product. These products may be dried at the acidic pH at which they were prepared or may be adjusted in pH before drying. Also described is the preparation of an acid soluble protein product, which may be an isolate, and which provides acidic solutions of improved clarity and is derived from the acidified pulse protein solution.

4 Claims, 2 Drawing Sheets

(56) References Cited

OTHER PUBLICATIONS

Anderson, R.L. et al., "Compositional changes in trypsin inhibitors, phytic acid, saponins and isoflavones related to soybean processing," J. Nutr., 1995, pp. 581S-588S, 125(3 Suppl), American Society for Nutrition.
Bacon, J.R. et al., "Preparation of transparent pea protein gels: a comparison of isolation procedures," Int. J. Food Sci. Technol., 2007, pp. 527-537, 25(5), Wiley.
Berk, Z., "Technology of Production of Edible Flours and Protein Products From Soybeans," FAO Agricultural Services Bulletin No. 97, 1992, Food and Agriculture Organization of the United Nations Rome http://www.fao.org/docrep/t0532e/t0532e00.HTM.
Boye, J. et al., "Pulse proteins: Processing, characterization, functional properties and applications in food and feed," Food. Res. Int., 2010, pp. 414-431, 43(2), Elsevier Ltd.
Chakraborty, P. et al., "Ultracentrifugation of salt-soluble proteins in ten legume species," J. Sci. Food Agric., 1979, pp. 766-771, 30(8), John Wiley & Sons, Ltd.
Damodaran, S. "Amino Acids, Peptides and Proteins," Food Chemistry, 1996, pp. 321-416, 3rd Edition, Marcel Dekker.
Doyle, J.J. et al., "The Glycosylated Seed Storage Proteins of Glycine max and Phaseolus vulgaris," J. Biol. Chem., 1986, pp. 9228-9238, 261(20), American Society of Biological Chemists, Inc.
Friedman, M. et al., "Nutritional and Health Benefits of Soy Proteins," J. Agri. Food Chem., 2001, pp. 1069-1086, 49(3), American Chemical Society.
Guillamon, E. et al., "The trypsin inhibitors present in seed of different grain legume species and cultivar," Food Chemistry, 2008, pp. 68-74, 107(1), Elsevier Ltd.
Haard, N.F. et al., Characteristics of Edible Plant Tissues, Food Chemistry, 1996, pp. 943-1011, 3rd Edition, Marcel Dekker.
Kagawa, H. et al., "Soybean basic 7 S globulin represents a protein widely distributed in legume species," FEBS Lett., 1987, pp. 145-149, 226(1), Elsevier Science Publishers B.V.

Marcone, M. "Biochemical and biophysical properties of plant storage proteins: a current understanding with emphasis on 11S seed globulins," Food Res. Int., 1999, pp. 79-92, 32(2), Elsevier Ltd.
Pedroche, J. et al., "Plant Protein Hydrolysates and Tailor-Made Foods," Electron. J. Environ. Agric. Food Chem., 2003, pp. 233-235, 2(1).
Sumner, A.K. et al., "Production and Evaluation of Pea Protein Isolate," J. Food Sci., 1981, pp. 364-366, 46(2), John Wiley and Sons.
Tomoskozi, S. et al., "Isolation and study of the functional properties of pea proteins," Nahrung/Food, 2001, pp. 399-401, 45(6), Wiley-VCH.
Vose, J.R., "Production and Functionality of Starches and Protein Isolates from Legume Seeds (Field Peas and Horsebeans)," Cereal Chem., 1980, pp. 406-410, 57(6), American Association of Cereal Chemists, Inc.
Wang, N. et al., "The Chemical Composition and Nutritive Value of Canadian Pulses," Canadian Grain Commission, Grain Research Laboratory, 2004.
Wilson, L.A. et al., "Isolation and Characterization of Starch from Mature Soybeans," Cereal Chem. 1978, pp. 661-670, 55(5), American Association of Cereal Chemists.
Wright, D.J. et al., "Legume proteins in food technology," Phil. Trans. R. Soc. Lond. B, 1984, pp. 381-393, 304(1120), The Royal Society.
Food and Agriculture Organization of the United Nations, Joint FAO/WHO Food Standards Programme, Codex Alimentarius: Cereals, Pulses, Legumesand Vegetable Proteins, 2007, 1st Edition, Food & Agriculture Org.
"U.S. Department of Agriculture,""Composition of Foods Raw, Processed, Prepared,""Agricultural Research Service, 2013, USDA National Nutrient Database for Standard Reference, Release 26. Nutrient Data Laboratory Home Page, http://www.ars.usda.gov/ba/bhnrc/ndl".

* cited by examiner

PREPARATION OF PULSE PROTEIN PRODUCTS (YP810)

CROSS-REFERENCE TO RELATED APPLICATIONS

This application claims priority to U.S. Provisional Patent Application No. 62/029,686, filed Jul. 28, 2014. The content of this application is incorporated herein by reference in its entirety.

FIELD OF THE INVENTION

The present invention relates to novel and inventive methods of preparing pulse protein products and to novel and inventive pulse protein products.

BACKGROUND TO THE INVENTION

In U.S. patent application Ser. No. 13/103,528 filed May 9, 2011 (US Patent Publication No. 2011-0274797 published Nov. 10, 2011), Ser. No. 13/289,264 filed Nov. 4, 2011 (US Patent Publication No. 2012-0135117 published May 31, 2012), Ser. No. 13/556,357 filed Jul. 24, 2012 (US Patent Publication No. 2013-0189408 published Jul. 25, 2013) and Ser. No. 13/642,003 filed Jan. 7, 2013 (US Patent Publication No. 2013-0129901 published May 23, 2013), ("YP701"), assigned to the assignee hereof and the disclosures of which are incorporated herein by reference, there are described procedures for the preparation of pulse protein products with excellent solubility and optionally clarity in low pH solutions as well as a clean flavour without pea/vegetable notes. The clean flavour of these products is a commercially valuable attribute.

In U.S. patent application Ser. No. 13/937,266 filed Jul. 9, 2013 (US Patent Publication No. 2014-0017379 published Jan. 16, 2014) ("YP701N2"), assigned to the assignee hereof and the disclosure of which is incorporated herein by reference, there is described the provision of near neutral pH forms of the pulse protein products described above. These products, with their clean taste, are useful for use in food compositions having a near neutral pH. Although solubility is still desirable, food applications at near neutral pH are typically not transparent and so complete solubility and clarity in water are not necessarily a requirement.

In the procedures described in the aforementioned U.S. patent application Ser. Nos. 13/103,528, 13/289,264, 13/556,357, 13/642,003 and 13/937,266, protein extraction is effected with calcium salt solution. The calcium salt solution assists in solubilisation of protein from the protein source while separating it from phytic acid, which is precipitated and removed from the protein solution. The protein solution is then optionally diluted with water and adjusted in pH to about 1.5 to about 4.4 to provide a preferably clear, acidified protein solution. While not wishing to be bound by any particular theory, it is thought that the clean flavour of the pulse protein products obtained by these procedures is promoted by the low pH treatment of the sample, preferably in combination with optional subsequent membrane processing steps.

In U.S. patent application Ser. No. 14/203,700 filed Mar. 11, 2014 (US Patent Publication No. 2014-0256914 published Sep. 11, 2014), assigned to the assignee hereof and the disclosure of which is incorporated herein by reference, there is described the provision of pulse protein products having a protein content of at least about 50 wt % resulting from the clarification of the protein solution after the calcium salt solution extraction described in the aforementioned U.S. patent application Ser. Nos. 13/103,528, 13/289,264, 13/556,357, 13/642,003 and 13/937,266. Such products may be comprised of fine solids captured by a disc stack centrifuge following extraction of pulse protein source with calcium salt solution and separation of the bulk of the residual pulse protein source with a decanter centrifuge. Alternatively, the products may be comprised of fine solids captured by a disc stack centrifuge following extraction of pulse protein source with water, separation of the bulk of the residual pulse protein source with a decanter centrifuge and calcium salt addition to the partially clarified protein solution.

One potential concern with the procedures described in the aforementioned U.S. patent application Ser. Nos. 13/103,528, 13/289,264, 13/556,357, 13/642,003, 13/937,266 and 14/203,700 may be the quantity of calcium salt required to effect the protein extraction step and the costs and issues of the quantity of salt entering the process as well as the recovery or disposal of calcium salts in the waste streams of the process. A reduction or elimination of calcium salt could result in significant savings in the cost of processing and production of the protein products.

SUMMARY OF THE INVENTION

The present invention relates to novel and inventive processes for the preparation of pulse protein products very low in, or substantially free of, pea/vegetable flavour notes, which do not include the use of calcium or other salt in extraction of the protein from the protein source material.

Accordingly, in one aspect of the present invention, there is provided a method of producing a pulse protein product having a protein content of at least about 60 wt %, preferably at least about 90 wt % (N×6.25) on a dry basis, which comprises:

(a) extracting a pulse protein source with water to cause solubilization of pulse protein from the protein source and to form an aqueous pulse protein solution, (b) at least partially separating the aqueous pulse protein solution from residual pulse protein source, (c) adjusting the pH of the aqueous pulse protein solution to a pH of about 1.5 to about 3.4 to produce an acidified pulse protein solution, (d) separating the acid insoluble solid material from the acidified pulse protein solution, (e) optionally concentrating the acidified pulse protein solution by a selective membrane technique, (f) optionally diafiltering the optionally concentrated acidified pulse protein solution, and (g) optionally drying the optionally concentrated and optionally diafiltered pulse protein solution.

In an embodiment of the present invention, when prepared at a low pH, the product is highly soluble in aqueous solutions having low pH and is well suited for use in food applications having a low pH such as acidic beverages. In another embodiment of the present invention, the pH of the acidified pulse protein solution or the optionally concentrated and optionally diafiltered acidified pulse protein solution may be adjusted to less than about 8.0, prior to the optional drying. In another embodiment of the present invention, the pH of the acidified pulse protein solution or the optionally concentrated and optionally diafiltered acidified pulse protein solution may be adjusted to about 6.0 to about 8.0, prior to the optional drying. In another embodiment of the present invention, the pH of the acidified pulse protein solution or the optionally concentrated and optionally diafiltered acidified pulse protein solution may be adjusted to about 6.5 to about 7.5, prior to the optional drying. In another embodiment of the present invention, when the product is provided at near neutral pH, it is in a form suited for use in neutral, or near-neutral, food applications, such as neutral beverages or bars.

Alternatively, the acidified pulse protein solution of the present invention may be membrane processed so as to provide a first acidic pulse protein product very low in, or substantially free of, pea/vegetable flavour notes that is highly soluble in aqueous solutions having low pH and provides low pH aqueous solutions of improved clarity for use in acidic beverages. A second pulse protein product, also very low in, or substantially free of, pea/vegetable flavour notes is also generated that may be used in acidic, neutral or near-neutral food applications.

Accordingly, in another aspect of the present invention, there is provided a method of producing a pulse protein product having a protein content of at least about 60 wt %, preferably at least about 90 wt % (N×6.25) on a dry basis, which comprises:

(a) extracting a pulse protein source with water to cause solubilization of pulse protein from the protein source and to form an aqueous pulse protein solution, (b) at least partially separating the aqueous pulse protein solution from residual pulse protein source, (c) adjusting the pH of the aqueous pulse protein solution to a pH of about 1.5 to about 3.4 to produce an acidified pulse protein solution, (d) separating the acid insoluble solid material from the acidified pulse protein solution, (e) concentrating and/or diafiltering the acidified pulse protein solution by a selective membrane technique to fractionate the protein components of the acidified pulse protein solution in a first retentate and a first permeate, (f) optionally drying the first retentate to provide a first pulse protein product, (g) concentrating and optionally diafiltering the first permeate to provide a second retentate and a second permeate, and (h) optionally drying the second retentate to provide a second pulse protein product.

In an embodiment of the present invention, the first retentate comprises the higher molecular weight protein species from the acidified pulse protein solution and the first permeate comprises the lower molecular weight protein species and contaminants from the acidified pulse protein solution. In another embodiment of the present invention, the first pulse protein product comprises higher molecular weight proteins derived from the acidified pulse protein solution. In another embodiment of the present invention, the concentration and optional diafiltration of the first permeate retains the lower molecular weight protein species in the second retentate and permits contaminants to pass into the second permeate.

In an embodiment of the present invention, the pH of the first retentate may be adjusted to less than about 8.0, prior to the optional drying step. In another embodiment of the present invention, the pH of the first retentate may be adjusted to about 6.0 to about 8.0, prior to the optional drying step. In another embodiment of the present invention, the pH of the first retentate may be adjusted to about 6.5 to about 7.5, prior to the optional drying step. When the product is provided at near neutral pH it is in a form suited for use in neutral or near-neutral food applications such as neutral beverages or bars.

In an embodiment of the present invention, the acid insoluble solid material arising in either aspect of the present invention mentioned above may be further processed to provide another pulse protein product. This product may generally have lower purity and a higher level of pea/vegetable flavour notes compared to the products derived from the acidified pulse protein solution. However, the flavour of the product derived from the acid insoluble solid material is such that it is still suitable for use in food and beverage applications.

Accordingly, in another aspect of the present invention, there is provided a method of producing a pulse protein product having a protein content of at least about 60 wt % (N×6.25) on a dry basis, which comprises optionally drying the acid insoluble solid material after optionally adjusting the pH to a value selected from the group consisting of less than about 8.0, about 6.0 to about 8.0 and about 6.5 to about 7.5, or preferably optionally drying the acid insoluble solid material after washing it with about 1 to about 20 volumes of water having the same pH as the acid insoluble solid material and optionally adjusting the pH to a value selected from the group consisting of less than about 8.0, about 6.0 to about 8.0 and about 6.5 to about 7.5.

Accordingly, in another aspect of the present invention, there is provided a process of producing a pulse protein product having a protein content of at least about 60 wt % (N×6.25) on a dry weight basis, which comprises:

(a) extracting a pulse protein source with water to cause solubilization of pulse protein from the protein source and to form an aqueous pulse protein solution, (b) at least partially separating the aqueous pulse protein solution from residual pulse protein source, (c) adjusting the pH of the aqueous pulse protein solution to a pH of about 1.5 to about 3.4 to produce an acidified pulse protein solution, (d) separating the acid insoluble solid material from the acidified pulse protein solution, and alternatively:

(e) optionally concentrating the acidified pulse protein solution by a selective membrane technique, (f) optionally diafiltering the optionally concentrated pulse protein solution, and (g) optionally drying the optionally concentrated and optionally diafiltered pulse protein solution, Or (h) concentrating and/or diafiltering the acidified pulse protein solution by a selective membrane technique to fractionate the protein component of the acidified pulse protein solution into a first retentate and a first permeate, (i) optionally drying the first retentate to provide a first pulse protein product, (j) concentrating and optionally diafiltering the first permeate to provide a second retentate and a second permeate, and (k) optionally drying the second retentate to provide a second pulse protein product.

In an embodiment of the present invention, the first retentate comprises the higher molecular weight protein species from the acidified pulse protein solution and the first permeate comprises the lower molecular weight protein species and contaminants from the acidified pulse protein solution. In another embodiment of the present invention, the first pulse protein product comprises higher molecular weight proteins derived from the acidified pulse protein solution. In another embodiment of the present invention, the concentration and optional diafiltration of the first permeate retains the lower molecular weight protein species in the second retentate and permits contaminants to pass into the second permeate. In another embodiment of the present invention, the second pulse protein product comprises lower molecular weight protein species derived from the acidified pulse protein solution. In another embodiment of the present invention, the second pulse protein product has improved clarity in acidic solution compared with the product derived from the acidified pulse protein solution without employing the fractionation step.

In an embodiment of the present invention, the acid insoluble solid material is optionally dried to form a pulse protein product having a protein content of at least about 60 wt % (N×6.25), on a dry weight basis.

In an embodiment of the present invention, the pH of the acid insoluble material is adjusted to less than about 8.0, prior to the optional drying step. In another embodiment of the present invention, the pH of the acid insoluble material is adjusted to about 6.0 to about 8.0, prior to the optional drying step. In another embodiment of the present invention, the pH of the acid insoluble material is adjusted to about 6.5 to about 7.5, prior to the optional drying step.

In an embodiment of the present invention, the acid insoluble solid material is washed by mixing with about 1 to about 20 volumes of water having a pH selected from the group consisting of about 1.5 to about 3.4 and about the same as the pH of the acid insoluble material, then is separated from the wash water prior to the optional drying step.

In an embodiment of the present invention, the pH of the washed acid insoluble material is adjusted to less than about 8.0, prior to the optional drying step. In another embodiment of the present invention, the pH of the washed acid insoluble material is adjusted to about 6.0 to about 8.0, prior to the optional drying step. In another embodiment of the present invention, the pH of the washed acid insoluble material is adjusted to and about 6.5 to about 7.5, prior to the optional drying step.

In an embodiment of the present invention, the wash water is combined with the acidified pulse protein solution of the separating step (d) and processed as in step (e), (f) and/or (g).

In an embodiment of the present invention, the wash water is combined with the acidified pulse protein solution of the separating step (d) and processed as in step (h), (i), (j) and/or (k).

In an embodiment of the present invention, the extraction step (a) is effected at a temperature of about 1° to about 100° C. In another embodiment of the present invention, the extraction step (a) is effected at a temperature of about 15° to about 65° C. In another embodiment of the present invention, the extraction step (a) is effected at a temperature of about 20° to about 35° C.

In an embodiment of the present invention, the water used for the extraction contains a pH adjusting agent so that the extraction is conducted at a pH of about 6 to about 11. In another embodiment of the present invention, the water used for the extraction contains a pH adjusting agent so that the extraction is conducted at a pH of about 6 to about 8.5. In another embodiment of the present invention, the pH adjusting agent is sodium hydroxide.

In an embodiment of the present invention, the aqueous pulse protein solution has a protein concentration of about 5 to about 50 g/L. In another embodiment of the present invention, the aqueous pulse protein solution has a protein concentration of about 10 to about 50 g/L.

In an embodiment of the present invention, the water contains an antioxidant.

In an embodiment of the present invention, following the separation step (b) and prior to the acidification step (c), the aqueous pulse protein solution is treated with an adsorbent to remove colour and/or odour compounds from the aqueous protein solution.

In an embodiment of the present invention, the pH of said aqueous pulse protein solution is adjusted in the acidifying step (c) to about 2.0 to about 3.0.

In an embodiment of the present invention, the acidified aqueous protein solution following separating step (d) is subjected to a heat treatment step. In an embodiment of the present invention, the heat treatment step is effected to inactivate heat-labile anti-nutritional factors. In an embodiment of the present invention, the anti-nutritional factors are heat-labile trypsin inhibitors. In another embodiment of the present invention, the heat treatment step is effected to pasteurize the acidified aqueous protein solution.

In an embodiment of the present invention, the heat treatment is effected at a temperature of about 70° to about 160° C. for about 10 seconds to about 60 minutes. In another embodiment of the present invention, the heat treatment is effected at a temperature of about 80° to about 120° C. for about 10 seconds to about 5 minutes. In another embodiment of the present invention, the heat treatment is effected at a temperature of about 85° to about 95° C. for about 30 seconds to about 5 minutes.

In an embodiment of the present invention, the heat treated acidified pulse protein solution is cooled to a temperature of about 2° to about 65° C. In another embodiment of the present invention, the heat treated acidified pulse protein solution is cooled to a temperature of about 50° to about 60° C.

In an embodiment of the present invention, the acidified aqueous pulse protein solution is dried to provide a pulse protein product having a protein content of at least about 60 wt % (N×6.25) d.b.

In an embodiment of the present invention, the acidified aqueous pulse protein solution is subjected to concentrating step (e) to produce a concentrated acidified pulse protein solution having a protein concentration of about 50 to about 300 g/L. In an embodiment of the present invention, the concentrated acidified pulse protein solution is subjected to diafiltering step (f).

In an embodiment of the present invention, the concentrated acidified pulse protein solution has a protein concentration of about 100 to about 200 g/L.

In an embodiment of the present invention, the concentrating step (e) is effected by ultrafiltration using a membrane having a molecular weight cut-off of about 1,000 to about 1,000,000 daltons. In another embodiment of the present invention, the concentrating step (e) is effected by ultrafiltration using a membrane having a molecular weight cut-off of about 1,000 to about 100,000 daltons.

In an embodiment of the present invention, the diafiltration step (f) is effected using water or acidified water on the acidified aqueous pulse protein solution before or after partial or complete concentration thereof.

In an embodiment of the present invention, the diafiltration step (f) is effected using about 1 to about 40 volumes of diafiltration solution. In another embodiment of the present invention, the diafiltration step (f) is effected using about 2 to about 25 volumes of diafiltration solution.

In an embodiment of the present invention, the diafiltration step (f) is effected until no significant further quantities of contaminants or visible colour are present in the permeate.

In an embodiment of the present invention, the diafiltration step (f) is effected until the retentate has been sufficiently purified so as to provide a pulse protein isolate with a protein content of at least about 90 wt % (N×6.25) d.b.

In an embodiment of the present invention, the diafiltration step (f) is effected using a membrane having a molecular weight cut-off of about 1,000 to about 1,000,000 daltons. In another embodiment of the present invention, the diafiltration step (f) is effected using a membrane having a molecular weight cut-off of about 1,000 to about 100,000 daltons.

In an embodiment of the present invention, an antioxidant is present in the diafiltration medium during at least part of the diafiltration step (f).

In an embodiment of the present invention, the concentration step (e) and optional diafiltration step (f) are carried out at a temperature of about 2° to about 65° C. In another embodiment of the present invention, the concentration step (e) and optional diafiltration step (f) are carried out at a temperature of about 50° to about 60° C.

In an embodiment of the present invention, the acidified aqueous pulse protein solution is subjected to step (h) to produce a concentrated and optionally diafiltered acidified pulse protein solution (first retentate) having a protein concentration of about 50 to about 300 g/L. In another embodiment of the present invention, the acidified aqueous pulse protein solution is subjected to step (h) to produce a concentrated and optionally diafiltered acidified pulse protein solution (first retentate) having a protein concentration of about 100 to about 200 g/L.

In an embodiment of the present invention, the acidified aqueous pulse protein solution is subjected to step (h) by microfiltration using a membrane having a pore size of about 0.05 to about 0.1 μm. In another embodiment of the present invention, the acidified aqueous pulse protein solution is subjected to step (h) by microfiltration using a membrane having a pore size of about 0.08 to about 0.1 μm In an embodiment of the present invention, the acidified aqueous pulse protein solution is subjected to step (h) by ultrafiltration using a membrane having a molecular weight cut-off of about 10,000 to about 1,000,000 daltons. In another embodiment of the present invention, the acidified aqueous pulse protein solution is subjected to step (h) by ultrafiltration using a membrane having a molecular weight cut-off of about 100,000 to about 1,000,000 daltons.

In an embodiment of the present invention, the diafiltration step (h) is effected using water or acidified water on the acidified aqueous pulse protein solution before optional subsequent concentration or after partial or complete concentration thereof.

In an embodiment of the present invention, the diafiltration step (h) is effected using about 1 to about 40 volumes of diafiltration solution. In another embodiment of the present invention, the diafiltration step (h) is effected using about 2 to about 25 volumes of diafiltration solution.

In an embodiment of the present invention, the diafiltration step (h) is effected until the retentate has been sufficiently purified so as to provide a pulse protein isolate with a protein content of at least about 90 wt % (N×6.25) d.b.

In an embodiment of the present invention, an antioxidant is present in the diafiltration medium during at least part of the diafiltration step (h).

In an embodiment of the present invention, the concentration step and optional diafiltration step are carried out at a temperature of about 2° to about 65° C. In another embodiment of the present invention, the concentration step and optional diafiltration step are carried out at a temperature of about 50° to about 60° C.

In an embodiment of the present invention, the first permeate is subjected to step (j) to produce a concentrated and optionally diafiltered acidified pulse protein solution (second retentate) having a protein concentration of about 10 to about 300 g/L. In another embodiment of the present invention, the first permeate is subjected to step (j) to produce a concentrated and optionally diafiltered acidified pulse protein solution (second retentate) having a protein concentration of about the second retentate has a protein concentration of about 100 to about 200 g/L.

In an embodiment of the present invention, the concentration and optional diafiltration step is effected by ultrafiltration using a membrane having a molecular weight cut-off of about 1,000 to about 100,000 daltons. In another embodiment of the present invention, the concentration and optional diafiltration step is effected by ultrafiltration using a membrane having a molecular weight cut-off of about 1,000 to about 10,000 daltons.

In an embodiment of the present invention, the optional diafiltration step is effected using water or acidified water on the second retentate before or after partial or complete concentration thereof.

In an embodiment of the present invention, the diafiltration of the concentrating and optional diafiltering step (j) is effected using about 1 to about 40 volumes of diafiltration solution. In another embodiment, the diafiltration of the concentrating and optional diafiltering step (j) is effected using about 2 to about 25 volumes of diafiltration solution.

In an embodiment of the present invention, the diafiltration of the concentrating and optional diafiltering step (j) is effected until the retentate has been sufficiently purified so as to provide a pulse protein isolate with a protein content of at least about 90 wt % (N×6.25) d.b.

In an embodiment of the present invention, an antioxidant is present in the diafiltration medium during at least part of the diafiltration of the concentrating and optional diafiltering step (j).

In an embodiment of the present invention, the concentration and optional diafiltration step (j) are carried out at a temperature of about 2° to about 65° C. In another embodiment of the present invention, the concentration and optional diafiltration step (j) are carried out at a temperature of about 50° to about 60° C.

In an embodiment of the present invention, the diafiltered acidified pulse protein solution is subjected to a heat treatment step. In an embodiment of the present invention, the heat treatment step is effected to inactivate heat labile anti-nutritional factors, including heat labile trypsin inhibitors.

In an embodiment of the present invention, the partially concentrated or concentrated and optionally diafiltered acidified pulse protein solution is subjected to a heat treatment step. In an embodiment of the present invention, the heat treatment step is effected to inactivate heat-labile anti-nutritional factors, including heat-labile trypsin inhibitors.

In an embodiment of the present invention, the heat treatment is effected at a temperature of about 70° to about 160° C. for about 10 seconds to about 60 minutes. In another embodiment of the present invention, the heat treatment is effected at a temperature of about 80° to about 120° C. for about 10 seconds to about 5 minutes. In another embodiment of the present invention, the heat treatment is effected at a temperature of about 85° C. to about 95° C. for about 30 seconds to about 5 minutes.

In an embodiment of the present invention, the heat treated pulse protein solution is cooled to a temperature of about 2° to about 65° C. In another embodiment of the present invention, the heat treated pulse protein solution is cooled to a temperature of about 50° to about 60° C.

In an embodiment of the present invention, the concentrated and optionally diafiltered acidified protein solution is treated with an adsorbent to remove colour and/or odour compounds.

In an embodiment of the present invention, the concentrated and optionally diafiltered acidified protein solution is pasteurized prior to drying.

In an embodiment of the present invention, the pasteurization step is effected at a temperature of about 55° to about 75° C. for about 15 seconds to about 60 minutes.

In an embodiment of the present invention, the optionally concentrated and optionally diafiltered acidified pulse protein solution is subjected to drying step (g) to provide a pulse protein isolate having a protein content of at least about 90 wt % (N×6.25) d.b. The Applicant has identified this pulse protein isolate as 810.

In an embodiment of the present invention, the concentrated and/or diafiltered acidified pulse protein solution of the first retentate is subjected to drying step (i) to provide a pulse protein isolate having a protein content of at least about 90 wt % (N×6.25) d.b. The Applicant has identified this pulse protein isolate as 816B.

In an embodiment of the present invention, the concentrated and optionally diafiltered acidified pulse protein solution of the second retentate is subjected to drying step (k) to provide a pulse protein isolate having a protein content of at least about 90 wt % (N×6.25) d.b. The Applicant has identified this pulse protein isolate as 816A.

In an embodiment of the present invention, the pH of the optionally concentrated and optionally diafiltered acidified pulse protein solution is adjusted to less than about 8.0, prior to optional drying step (g). In another embodiment of the present invention, the pH of the optionally concentrated and optionally diafiltered acidified pulse protein solution is adjusted to about 6.0 to about 8.0, prior to optional drying step (g). In another embodiment of the present invention, the pH of the optionally concentrated and optionally diafiltered acidified pulse protein solution is adjusted to about 6.5 to about 7.5, prior to optional drying step (g).

In an embodiment of the present invention, the pH of the membrane processed acidified pulse protein solution is adjusted to less than about 8.0, prior to drying step (i). In an embodiment of the present invention, the pH of the membrane processed acidified pulse protein solution is adjusted to about 6.0 to about 8.0, prior to drying step (i). In another embodiment of the present invention, the pH of the membrane processed acidified pulse protein solution is adjusted to and about 6.5 to about 7.5, prior to drying step (i).

In an embodiment of the present invention, the concentration and/or optional diafiltration step are operated in a manner favourable to the removal of trypsin inhibitors.

In an embodiment of the present invention, a reducing agent is present during the extraction step (a). In an embodiment of the present invention, the presence of the reducing agent during the extraction step (a) is intended to disrupt or rearrange the disulfide bonds of trypsin inhibitors to achieve a reduction in trypsin inhibitor activity.

In an embodiment of the present invention, a reducing agent is present during the optional concentration step (e) and/or the optional diafiltration step (f) or during the membrane processing step (h). In an embodiment of the present invention, the presence of the reducing agent is intended to disrupt or rearrange the disulphide bonds of trypsin inhibitors to achieve a reduction in trypsin inhibitor activity.

In an embodiment of the present invention, a reducing agent is added to the optionally concentrated optionally diafiltered pulse protein solution prior to the drying step (g) and/or the dried pulse protein product. In an embodiment of the present invention, the presence of the reducing agent is intended to disrupt or rearrange the disulphide bonds of trypsin inhibitors to achieve a reduction in trypsin inhibitor activity.

In an embodiment of the present invention, a reducing agent is added to the membrane processed pulse protein solution prior to the drying step (i) and/or the dried pulse protein product. In an embodiment of the present invention, the presence of the reducing agent is intended to disrupt or rearrange the disulphide bonds of trypsin inhibitors to achieve a reduction in trypsin inhibitor activity.

In an embodiment of the present invention, a reducing agent is added to the concentrated optionally diafiltered pulse protein solution prior to the drying step (k) and/or the dried pulse protein product. In an embodiment of the present invention, the presence of the reducing agent is intended to disrupt or rearrange the disulphide bonds of trypsin inhibitors to achieve a reduction in trypsin inhibitor activity.

Accordingly, in another aspect of the present invention, there is provided a pulse protein product having a protein content of at least about 60 wt % (N×6.25) d.b. and which is prepared without a process step involving the addition of salt, has little or no pea or vegetable flavour, and requires no enzymes in the production thereof. In an embodiment of the present invention, the pulse protein product contains more than about 1.5 wt % d.b. phytic acid. In another embodiment of the present invention, the pulse protein product has a protein content of at least about 90 wt % (N×6.25) d.b. In another embodiment of the present invention, the pulse protein product is completely soluble in aqueous media at acid pH values of less than about 4.0. In another embodiment of the present invention, the pulse protein product is completely soluble in aqueous media at acid pH values of less than about 3.0. In another embodiment of the present invention, the pulse protein product does not require stabilizers or other additives to maintain the protein product in solution or suspension. In another embodiment of the present invention, the pulse protein product is blended with water-soluble powdered materials for the production of aqueous solutions of the blend. In another embodiment of the present invention, the pulse protein product is a powdered beverage.

Accordingly, in another aspect of the present invention, there is provided an aqueous solution of the pulse protein product as described above. In an embodiment of the present invention, the aqueous solution is a beverage. In another embodiment of the present invention, the beverage is a clear beverage in which the pulse protein product is completely soluble and substantially transparent. In another embodiment of the present invention, the beverage is not a clear beverage and in which the dissolved pulse protein does not increase the haze level. In another embodiment of the present invention, the beverage is not a clear beverage and in which the dissolved pulse protein contributes to the haze level of the beverage. In another embodiment of the present invention, the pulse protein product has a low trypsin inhibitor activity.

Accordingly, in another aspect of the present invention, there is provided a pulse protein product having a protein content of at least about 60 wt % (N×6.25) d.b., and a protein solubility at 1% protein w/v in water at a pH of about 2 to about 3 of greater than about 90%, and a protein solubility at 1% protein w/v in water at a pH of about 4 to about 6 of less than about 35% and a protein solubility at 1% protein w/v in water at a pH of about 7 of between about 25% and 55%. In an embodiment of the present invention, the solubility of the pulse protein product is determined by the method of Example 9. In another embodiment of the present invention, the pulse protein product is a yellow pea protein product.

Accordingly, in another aspect of the present invention, there is provided a pulse protein product having a protein content of at least about 60 wt % (N×6.25) d.b., and a protein solubility at 1% protein w/v in water at a pH of about 2 of between about 35% and 75%, and a protein solubility at 1% protein w/v in water at a pH of about 3 of between about 25% and 55%, and a protein solubility at 1% protein w/v in water at a pH of about 4 of between about 15% and 30%, and a protein solubility at 1% protein w/v in water at a pH of about 7 of between about 15% and 50%. In an embodiment of the present invention, the solubility of the pulse protein product is determined by the method of Example 9. In another embodiment of the present invention, the pulse protein product is a yellow pea protein product.

Accordingly, in another aspect of the present invention, there is provided a pulse protein product having a molecular weight profile comprising: about 7 to about 20% greater than about 100,000 Da, about 13 to about 40% from about 15,000 to about 100,000 Da, about 15 to about 28% from about 5,000 to about 15,000 Da, and about 21 to about 57% from about 1,000 to about 5,000 Da. In an embodiment of the present invention, the molecular weight profile of the pulse protein product is determined by the method of Example 10. In another embodiment of the present invention, the pulse protein product is a yellow pea protein product.

Accordingly, in another aspect of the present invention, there is provided a pulse protein product having a molecular weight profile comprising: about 12 to about 27% greater than about 100,000 Da, about 18 to about 35% from about 15,000 to about 100,000 Da, about 20 to about 37% from about 5,000 to about 15,000 Da, and about 12 to about 43% from about 1,000 to about 5,000 Da. In an embodiment of the present invention, the molecular weight profile of the pulse protein product is determined by the method of Example 10. In another embodiment of the present invention, the pulse protein product is a yellow pea protein product.

Accordingly, in another aspect of the present invention, there is provided a pulse protein product having a molecular weight profile comprising: about 4 to about 8% greater than about 100,000 Da, about 32 to about 36% from about 15,000 to about 100,000 Da, about 43 to about 48% from about 5,000 to about 15,000 Da, and about 12 to about 16% from about 1,000 to about 5,000 Da. In an embodiment of the present invention, the molecular weight profile of the pulse protein product is determined by the method of Example 10. In another embodiment of the present invention, the pulse protein product is a yellow pea protein product.

Accordingly, in another aspect of the present invention, there is provided a pulse protein product having a molecular weight profile comprising: about 8 to about 12% greater than about 100,000 Da, about 16 to about 27% from about 15,000 to about 100,000 Da, about 13 to about 21% from about 5,000 to about 15,000 Da, and about 43 to about 57% from about 1,000 to about 5,000 Da. In an embodiment of the present invention, the molecular weight profile of the pulse protein product is determined by the method of Example 10. In another embodiment of the present invention, the pulse protein product is a yellow pea protein product.

Accordingly, in another aspect of the present invention, there is provided a pulse protein product having a protein content of at least about 60 wt % (N×6.25) d.b., and a protein solubility at 1% protein w/v in water at a pH of about 2 to about 7 of less than about 40%, and a phytic acid content of greater than about 3.0% d.b. In an embodiment of the present invention, the solubility of the pulse protein product is determined by the method of Example 9. In another embodiment of the present invention, the pulse protein product is a yellow pea protein product.

Accordingly, in another aspect of the present invention, there is provided a pulse protein product having a protein content of at least about 60 wt % (N×6.25) d.b., and a protein solubility at 1% protein w/v in water at a pH of about 2 to about 7 of less than about 30%, and an acid hydrolysable carbohydrate content of greater than 6% d.b. In an embodiment of the present invention, the solubility of the pulse protein product is determined by the method of Example 9. In another embodiment of the present invention, the acid hydrolysable carbohydrate content is determined by the method of Example 12. In another embodiment of the present invention, the pulse protein product is a yellow pea protein product.

Accordingly, in another aspect of the present invention, there is provided a pulse protein product having a protein content of at least about 60 wt % (N×6.25) d.b., and a protein solubility at 1% protein w/v in water at a pH of about 2 to about 4 of greater than about 90%, and an acid hydrolysable carbohydrate content of greater than 6% d.b. In an embodiment of the present invention, the solubility of the pulse protein product is determined by the method of Example 9. In another embodiment of the present invention, the acid hydrolysable carbohydrate content is determined by the method of Example 12. In another embodiment of the present invention, the pulse protein product is a yellow pea protein product.

Accordingly, in another aspect of the present invention, there is provided a pulse protein product having a protein content of at least about 60 wt % (N×6.25) d.b., prepared without the addition of salt or enzyme hydrolysis, which has a haze reading for a solution prepared by dissolving sufficient protein powder to supply 0.48 g of protein in 15 ml of water, selected from the group consisting of less than 30% and less than 20%. The Applicant has identified this pulse protein product as 816A. In an embodiment of the present invention, the salt is a calcium salt. In another embodiment of the present invention, the pulse protein product is a yellow pea protein product.

The pulse protein products produced according to the processes disclosed herein are suitable for use in a wide variety of conventional applications of protein products, including but not limited to protein fortification of processed foods and beverages and as functional ingredients in foods and beverages. Other uses of the pulse protein products produced according to the processes disclosed herein are in pet foods, animal feed and in industrial and cosmetic applications and in personal care products.

GENERAL DESCRIPTION OF THE INVENTION

Figure 1:
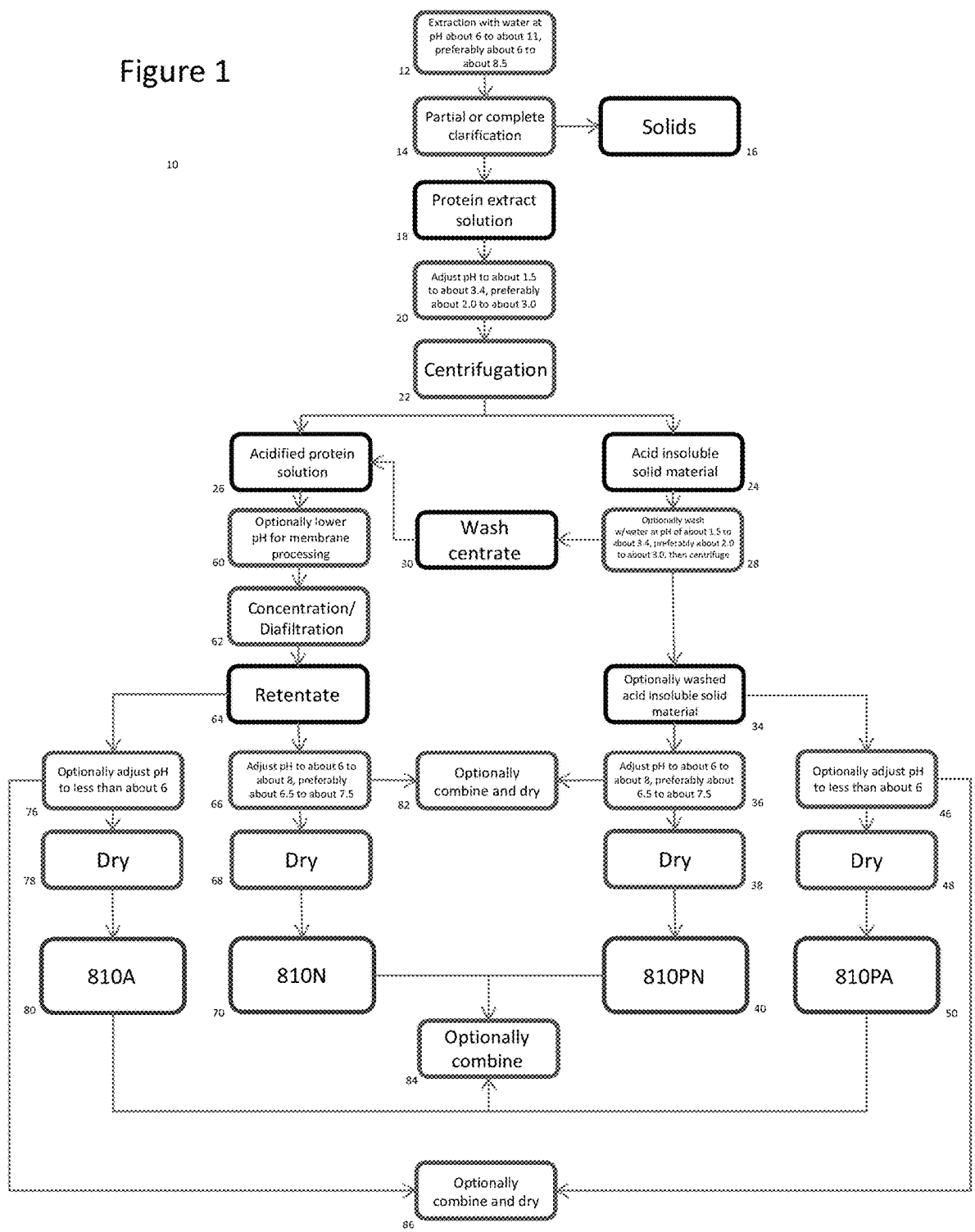
FIG. 1 is a schematic flow sheet illustrating an embodiment of the process of the present invention.

The initial step of the process of providing the pulse protein products of the present invention involves solubilizing pulse protein from a pulse protein source. The pulses to which the present invention may be applied include, but are not limited to, lentils, chickpeas, dry peas and dry beans. The pulse protein source may be pulses or any pulse product or by-product derived from the processing of pulses. For example, the pulse protein source may be a flour prepared by grinding an optionally dehulled pulse. As another example, the pulse protein source may be a protein-rich pulse fraction formed by dehulling and grinding a pulse and then air classifying the dehulled and ground material into starch-rich and protein-rich fractions. The pulse protein product recovered from the pulse protein source may be the protein naturally occurring in pulses or the proteinaceous material may be a protein modified by genetic manipulation but possessing characteristic hydrophobic and polar properties of the natural protein.

The pulse protein products of the present invention may be prepared from pulse protein source by either a batch process or a continuous process or a semi-continuous process. Protein solubilisation from the pulse protein source material is effected using water. The water used may be tap water or water having different levels of purity. In an embodiment of the present invention, reverse osmosis (RO) purified water is preferred.

The pH of the extraction may be about 6 to about 11, preferably about 6.5 to about 8.5. Food grade sodium hydroxide or potassium hydroxide or other suitable food grade alkali may be added to the water to adjust the pH of the extraction as required. The solubilization of the protein is effected at a temperature of from about 1° to about 100° C., preferably about 15° to about 65° C., more preferably about 20° to about 35° C., preferably accompanied by agitation to decrease the solubilisation time, which is usually about 1 to about 60 minutes. The temperature of the extraction should be such that the viscosity of the slurry of pulse protein source in water does not significantly impair mixing or pumpability. In an embodiment of the present invention, it is preferred to effect the solubilization to extract substantially as much protein form the pulse protein source as is practicable, so as to provide an overall high product yield.

Extraction of the protein from the pulse protein source, when conducted in a continuous operation, is carried out in any manner consistent with effecting a continuous extraction of protein from the pulse protein source. In one embodiment, the pulse protein source is continuously mixed with the water and the mixture is conveyed through a pipe or conduit having a length and at a flow rate for a residence time sufficient to effect the desired extraction in accordance with the parameters described herein.

The concentration of pulse protein source in the water during the solubilisation step may vary widely. Typical concentration values are about 5 to about 20% w/v.

The protein extraction step has the additional effect of solubilizing fats which may be present in the pulse protein source, which then results in the fats being present in the aqueous phase.

The protein solution resulting from the extraction step generally has a protein concentration of about 5 to about 50 g/L, preferably about 10 to about 50 g/L.

The water may contain an antioxidant. The antioxidant may be any conventional antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of any phenolics in the protein solution.

The aqueous phase resulting from the extraction step then may be separated from the bulk of the residual pulse protein source, in any conventional manner, such as by employing a decanter centrifuge. Preferably, the finer residual pulse protein source material is left in the pulse protein solution, but if desired, these finer solids may be removed by disc centrifugation and/or filtration. The separation step may be conducted at any temperature within the range of about 1° to about 100° C., preferably about 15° to about 65° C., more preferably about 20° to about 35° C. The temperature of the separation step should be such that the viscosity of the slurry of pulse protein source in water does not significantly impede the separation step. The separated residual pulse protein source material may be dried for disposal or further processed, such as to recover starch and/or residual protein. Residual protein may be recovered by re-extracting the separated residual pulse protein source with fresh water and the protein solution yielded upon clarification combined with the initial protein solution for further processing as described below. A counter-current extraction procedure may also be utilized. The separated residual pulse protein source may alternatively be processed by any other conventional procedure to recover residual protein.

The aqueous pulse protein solution may be treated with an anti-foamer, such as any suitable food-grade, non-silicone based anti-foamer, to reduce the volume of foam formed upon further processing. The quantity of anti-foamer employed is generally greater than about 0.0003% w/v. Alternatively, the anti-foamer in the quantity described may be added in the extraction steps.

The separated aqueous pulse protein solution may be subject to a defatting operation, if desired or required. Defatting of the separated aqueous pulse protein solution may be achieved by any conventional procedure.

The aqueous pulse protein solution may be treated with an adsorbent, such as granulated activated carbon, to remove colour and/or odour compounds. Such adsorbent treatment may be carried out under any conventional conditions, generally at the ambient temperature of the separated aqueous protein solution.

The pulse protein solution is then adjusted in pH to a value of about 1.5 to about 3.4, preferably about 2.0 to about 3.0, by the addition of any suitable food grade acid, such as hydrochloric acid or phosphoric acid. For pulse proteins, isoelectric precipitation typically is performed at about pH 4.5. By adjusting the pH to lower values in the process of the present invention, a greater portion of the proteins, preferably a significant portion of the proteins, such as about 35 wt % or more, preferably about 60 wt % or more, more preferably about 80 wt % or more, of the protein is soluble in the acidified solution. The remaining protein is contained in what is termed the acid insoluble solid material, which is removed from the acidified pulse protein solution by any conventional means, such as by the use of a disc stack centrifuge and further processed as described below. The pH adjustment may be done at any conventional temperature and in one embodiment of the present invention, preferably the temperature of the pulse protein solution for pH adjustment is 20° to 35° C. If desired, the pulse protein solution may be diluted with water prior to the acidification step described above.

If desired or required, the pH of the acidified protein solution may be lowered further prior to further processing. The adjusted pH of the acidified protein solution should still be in the range of about 1.5 to about 3.4, preferably about 2.0 to about 3.0.

The acidified aqueous pulse protein solution may be subjected to a heat treatment to inactivate heat labile anti-nutritional factors, such as trypsin inhibitors, present in such solution as a result of extraction from the pulse protein source material during the extraction step. Such a heating step also provides the additional benefit of reducing the microbial load. Generally, the protein solution is heated to a temperature of about 70° to about 160° C., preferably about 80° to about 120° C., more preferably about 85° to about 95° C., for about 10 seconds to about 60 minutes, preferably about 10 seconds to about 5 minutes, more preferably about 30 seconds to about 5 minutes. The heat treated acidified pulse protein solution then may be cooled for further processing as described below, to a temperature of about 2° to about 65° C., preferably about 50° C. to about 60° C.

The resulting acidified aqueous pulse protein solution may be directly dried to produce a pulse protein product. In order to provide a pulse protein product having a decreased impurities content, such as a pulse protein isolate, the acidified aqueous pulse protein solution may be processed as described below prior to drying. Further processing as described below is also believed to have a beneficial effect on the flavour of the product.

The acidified aqueous pulse protein solution may be concentrated to provide a concentrated pulse protein solution having a protein concentration of about 50 to about 300 g/L, preferably about 100 to about 200 g/L.

The concentration step may be effected in any conventional manner consistent with batch or continuous operations, such as by employing any conventional selective membrane technique, such as ultrafiltration or diafiltration, using membranes, such as hollow-fibre membranes or spiral-wound membranes, with a suitable molecular weight cut-off, such as about 1,000 to about 1,000,000 daltons, preferably about 1,000 to about 100,000 daltons, having regard to differing membrane materials and configurations, and, for continuous operations, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include low molecular weight materials extracted from the source material, such as carbohydrates, pigments, low molecular weight proteins and anti-nutritional factors, such as trypsin inhibitors, which are themselves low molecular weight proteins. The molecular weight cut-off of the membrane is usually chosen to ensure retention of a significant proportion of the protein in the solution, while permitting contaminants to pass through having regard to the different membrane materials and configurations.

The concentrated pulse protein solution then may be subjected to a diafiltration step using water. The diafiltration water is preferably at a pH equal to that of the protein solution being diafiltered. Such diafiltration may be effected using from about 1 to about 40 volumes of diafiltration solution, preferably about 2 to about 25 volumes of diafiltration solution. In the diafiltration operation, further quantities of contaminants are removed from the aqueous pulse protein solution by passage through the membrane with the permeate. This purifies the aqueous protein solution and may also reduce its viscosity. The diafiltration operation may be effected until no significant further quantities of contaminants or visible colour are present in the permeate or until the retentate has been sufficiently purified so as, when dried, to provide a pulse protein isolate with a protein content of at least about 90 wt % (N×6.25) d.b. Such diafiltration may be effected using the same membrane as for the concentration step. However, if desired, the diafiltration step may be effected using a separate membrane with a different molecular weight cut-off, such as a membrane having a molecular weight cut-off in the range of about 1,000 to about 1,000,000 daltons, preferably about 1,000 to about 100,000 daltons, having regard to different membrane materials and configurations.

Alternatively, the diafiltration step may be applied to the acidified aqueous protein solution prior to concentration or to partially concentrated acidified aqueous protein solution. Diafiltration may also be applied at multiple points during the concentration process. When diafiltration is applied prior to concentration or to the partially concentrated solution, the resulting diafiltered solution may then be additionally concentrated. The viscosity reduction achieved by diafiltering multiple times as the protein solution is concentrated may allow a higher final, fully concentrated protein concentration to be achieved. This reduces the volume of material to be dried.

The concentration step and the diafiltration step may be effected herein in such a manner that the pulse protein product subsequently recovered contains less than about 90 wt % protein (N×6.25) d.b., such as at least about 60 wt % protein (N×6.25) d.b. By partially concentrating and/or partially diafiltering the aqueous pulse protein solution, it is possible to only partially remove contaminants. This protein solution may then be dried to provide a pulse protein product with lower levels of purity.

An antioxidant may be present in the diafiltration water during at least part of the diafiltration step. The antioxidant may be any conventional antioxidant, such as sodium sulfite or ascorbic acid. The quantity of antioxidant employed in the diafiltration water depends on the materials employed and may vary from about 0.01 to about 1 wt %, preferably about 0.05 wt %. The antioxidant serves to inhibit the oxidation of any phenolics present in the pulse protein solution.

The optional concentration step and the optional diafiltration step may be effected at any conventional temperature, generally about 2° to about 65° C., preferably about 50° to about 60° C., and for the period of time to effect the desired degree of concentration and diafiltration. The temperature and other conditions used to some degree depend upon the membrane equipment used to effect the membrane processing, the desired protein concentration of the solution and the efficiency of the removal of contaminants to the permeate.

As alluded to earlier, pulses contain anti-nutritional trypsin inhibitors. The level of trypsin inhibitor activity in the final pulse protein product can be controlled by the manipulation of various process variables.

As noted above, heat treatment of the acidified aqueous pulse protein solution may be used to inactivate heat-labile trypsin inhibitors. The partially concentrated or fully concentrated acidified pulse protein solution may also be heat treated to inactivate heat labile trypsin inhibitors. When the heat treatment is applied to the partially concentrated acidified pulse protein solution, the resulting heat treated solution may then be additionally concentrated.

In addition, the concentration and/or diafiltration steps may be operated in a manner favourable for removal of trypsin inhibitors in the permeate along with the other contaminants. Removal of the trypsin inhibitors is promoted by using a membrane of larger pore size, such as 30,000 to 1,000,000 Da, operating the membrane at elevated temperatures, such as about 30° to about 65° C., preferably about 50° to about 60° C. and employing greater volumes of diafiltration medium, such as 10 to 40 volumes.

Acidifying and membrane processing the pulse protein solution at a lower pH, such as about 1.5 to about 3, may reduce the trypsin inhibitor activity relative to processing the solution at higher pH, such as about 3 to about 3.4. When the protein solution is concentrated and/or diafiltered at the low end of the pH range, it may be desired to raise the pH of the solution prior to drying. The pH of the concentrated and/or diafiltered protein solution may be raised to the desired value, for example a pH of about 3, by the addition of any conventional food grade alkali, such as sodium hydroxide.

Further, a reduction in trypsin inhibitor activity may be achieved by exposing pulse materials to reducing agents that disrupt or rearrange the disulfide bonds of the inhibitors. Suitable reducing agents include, but are not limited to, sodium sulfite, cysteine and N-acetylcysteine.

The addition of such reducing agents may be effected at various stages of the overall process. The reducing agent may be added with the pulse protein source material in the extraction step, may be added to the aqueous pulse protein solution following removal of residual pulse protein source material, may be added to the diafiltered retentate before drying or may be dry blended with the dried pulse protein product. The addition of the reducing agent may be combined with the heat treatment step and membrane processing steps, as described above.

If it is desired to retain active trypsin inhibitors in the protein solution, this can be achieved by eliminating or reducing the intensity of the heat treatment step, not utilizing reducing agents, operating the optional concentration and optional diafiltration steps at the higher end of the pH range, such as about 3 to about 3.4, utilizing a concentration and diafiltration membrane with a smaller pore size, operating the membrane at lower temperatures and employing fewer volumes of diafiltration medium.

The optionally concentrated and optionally diafiltered protein solution may be subject to a further defatting operation, if desired or required. Defatting of the optionally concentrated and optionally diafiltered protein solution may be achieved by any conventional procedure.

The optionally concentrated and optionally diafiltered aqueous protein solution may be treated with an adsorbent, such as granulated activated carbon, to remove colour and/or odour compounds. Such adsorbent treatment may be carried out under any conventional conditions, generally at the ambient temperature of the protein solution.

The optionally concentrated and optionally diafiltered aqueous pulse protein solution may be pasteurized prior to drying or further processing. Such pasteurization may be effected under any conventional pasteurization conditions. Generally, the optionally concentrated and optionally diafiltered pulse protein solution is heated to a temperature of about 55° to about 75° C. for about 15 seconds to about 60 minutes. The pasteurized pulse protein solution then may be cooled, preferably to a temperature of about 25° to about 40° C.

The optionally concentrated, optionally diafiltered and optionally pasteurized pulse protein solution then may be dried by any conventional means such as spray drying or freeze drying to provide a pulse protein product. Alternatively, the optionally concentrated, optionally diafiltered and optionally pasteurized pulse protein solution may be adjusted in pH to a value of less than about 8.0, preferably about 6 to about 8, more preferably about 6.5 to about 7.5, prior to drying. The pH may be raised in any conventional manner such as by the addition of sodium hydroxide or potassium hydroxide solution. If the protein solution is not pasteurized before pH adjustment, the pasteurization may be conducted after the pH adjustment using the conditions described above.

The dry pulse protein product (prepared with or without the pH adjustment step prior to drying) has a protein content greater than about 60 wt %. Preferably, the dry pulse protein product is an isolate with a protein content in excess of about 90 wt % (N×6.25) d.b.

In accordance with another aspect of the present invention, the acid insoluble solid material captured after adjustment of the pH of the pulse protein solution to the range of about 1.5 to about 3.4, preferably about 2.0 to about 3.0, may be optionally diluted with RO water then may be dried to form a pulse protein product having a protein content of at least about 60 wt % (N×6.25) d.b. Alternatively, the pH of the optionally diluted acid insoluble solid material may be raised to a value less than about 8.0, preferably about 6.0 to about 8.0, more preferably about 6.5 to about 7.5 by any conventional means such as by the addition of sodium hydroxide solution or potassium hydroxide solution prior to optional drying to form a pulse protein product having a protein content of at least about 60 wt % (N×6.25) d.b. Preferably, the acid insoluble solid material is washed in order to remove contaminants and improve the purity and flavour of the product. The acid insoluble solid material may be washed by suspending the solids in between about 1 and about 20 volumes, preferably about 1 to about 10 volumes of RO water having a pH within the range of about 1.5 to about 3.4 and preferably matching the pH of the acid insoluble solid material. The washing step may be conducted at any conventional temperature such as about 20° to about 35° C. The acid insoluble solid material is mixed with the wash solution for any conventional length of time, preferably about 15 minutes or less. The washed acid insoluble solid material may then be separated from the acid wash solution by any conventional means such as by centrifugation using a disc stack centrifuge. The acid wash solution may be added to the acidified protein solution for further processing as discussed above. The washed acid insoluble solid material may be optionally diluted with RO water then may be dried by any conventional means such as spray drying or freeze drying to provide a pulse protein product having a protein content of at least about 60 wt % (N×6.25) d.b. Alternatively, the pH of the optionally diluted washed acid insoluble solid material may be adjusted to a value of less than about 8.0, preferably about 6.0 to about 8.0, more preferably about 6.5 to about 7.5 by any conventional means such as by the addition of sodium hydroxide solution or potassium hydroxide solution prior to optional drying. The flavour of products derived from the acid insoluble solid material may be generally higher in pea/vegetable notes compared to the products prepared by processing the acid soluble protein fraction. However, the flavour of the products derived from the acid insoluble solid material is such that the products are suitable for use in food and beverage applications.

A pasteurization step may be employed on the optionally diluted acid insoluble solid material or optionally diluted washed acid insoluble solid material prior to the optional drying step. Such pasteurization may be effected under any conventional pasteurization conditions. Generally, the optionally diluted acid insoluble solid material or optionally diluted washed acid insoluble solid material is heated to a temperature of about 55° to about 75° C. for about 15 seconds to about 60 minutes. The pasteurized optionally diluted acid insoluble solid material or optionally diluted washed acid insoluble solid material then may be cooled, preferably to a temperature of about 25° to about 40° C. If the optionally diluted acid insoluble solid material or optionally diluted washed acid insoluble solid material is not pasteurized before pH adjustment, the pasteurization may be conducted after the pH adjustment using the conditions described above.

In another aspect of the present invention, the membrane processing of the acidified aqueous pulse protein solution is conducted so to separate the higher molecular weight proteins from the lower molecular weight proteins which yield an acid soluble pulse protein product, prepared without the use of calcium salt, providing substantially clear aqueous pulse protein solutions. When this process alternative is employed, the acidified pulse protein solution is concentrated and/or diafiltered with the molecular weight cut-off of the concentration and diafiltration membranes chosen to permit the lower molecular weight proteins to pass to the permeate with the contaminants. Such concentration and diafiltration steps may be effected in any conventional manner consistent with batch or continuous operations, such as by employing any conventional selective membrane technique, such as microfiltration or ultrafiltration, using membranes, such as hollow-fibre membranes or spiral-wound membranes, with a suitable molecular weight cut-off, such as about 0.05 to about 0.1 µm, preferably about 0.08 to about 0.1 µm for microfiltration and about 10,000 to about 1,000,000 daltons, preferably about 100,000 to about 1,000,000 daltons for ultrafiltration, having regard to differing membrane materials and configurations, and, for continuous operations, dimensioned to permit the desired degree of concentration as the acidified aqueous protein solution passes through the membranes. In the concentration step, the acidified aqueous pulse protein solution is concentrated to a protein concentration of about 50 to about 300 g/L, preferably about 100 to about 200 g/L. The acidified pulse protein solution or partially concentrated acidified pulse protein solution or concentrated acidified pulse protein solution may be diafiltered with water, preferably at a pH equal to that of the protein solution being diafiltered. Such diafiltration may be effected using from about 1 to about 40 volumes of diafiltration solution, preferably about 2 to about 25 volumes of diafiltration solution. When the diafiltration is effected on the acidified pulse protein solution or partially concentrated pulse protein solution, the diafiltered solution may subsequently be additionally concentrated. The concentration and diafiltration steps may be effected at any conventional temperature, generally about 2° to about 65° C., preferably about 50° to about 60° C. The lower molecular weight proteins are captured in the permeate of the membrane processes along with other small molecule contaminants.

The lower molecular weight proteins are then separated from the contaminants by subsequent concentration of the protein solution (step 1 permeate) by membrane processing such as ultrafiltration to a protein concentration of about 10 to about 300 g/L, preferably about 100 to about 200 g/L and optional diafiltration, which may be carried out on the protein solution before or after complete concentration thereof. The optional diafiltration step is conducted using a diafiltration solution of water or acidified water, preferably having a pH the same as or lower than the protein solution. The concentration and diafiltration steps are performed using a membrane having a lower molecular weight cut-off such as about 1,000 to about 100,000 daltons, preferably 1,000 to about 10,000 daltons operated as described above.

This second membrane processing step may be effected in such a manner that the lower molecular weight pulse protein product recovered contains less than about 90 wt % protein (N×6.25) d.b., such as, for example, at least about 60 wt % protein (N×6.25) d.b. By partially concentrating and/or partially diafiltering the aqueous lower molecular weight pulse protein solution, it is possible to only partially remove contaminants. This protein solution may then be dried to provide a pulse protein product with lower levels of purity. The pulse protein product is prepared without the use of salt, is highly soluble and is able to produce substantially clear protein solutions under acidic conditions.

The concentrated and optionally diafiltered solution of lower molecular weight proteins or the retentate of the membrane fractionation process (which contains the higher molecular weight proteins) may be treated to reduce the activity of trypsin inhibitors as described above. The concentrated and optionally diafiltered solution of lower molecular weight proteins or the retentate of the membrane fractionation process (which contains the higher molecular weight proteins) may be pasteurized as described above.

The concentrated and optionally diafiltered solution of lower molecular weight proteins then may be dried by any convenient means such as spray drying or freeze drying to provide a pulse protein product. The dry pulse protein product has a protein content greater than about 60 wt % d.b. Preferably, the dry pulse protein product is an isolate with a protein content in excess of about 90 wt % (N×6.25) d.b.

Additional products may be obtained from the retentate of the membrane fractionation process, which contains the higher molecular weight proteins. This protein solution may be dried by any conventional means, with or without adjustment of the pH of the protein solution to a value of less than about 8.0, preferably about 6.0 to about 8.0, more preferably about 6.5 to about 7.5 using food grade alkali. The pasteurization step described above may be applied to the retentate of the membrane fractionation process after the pH adjustment step. The dry pulse protein product has a protein content greater than about 60 wt % d.b., preferably the dry pulse protein product is an isolate with a protein content in excess of about 90 wt % (N×6.25) d.b. Products obtained from the retentate of the membrane fractionation process are very low in, or substantially free of, pea/vegetable flavour notes.

Referring now to FIG. 1, which shows a process 10 according to one aspect of the present invention, a pulse protein source is subjected to an initial extraction with water at 12, at a pH of about 6 to about 11, preferably about 6.0 to about 8.5. The protein extract solution then is completely or partially clarified by the removal of residual pulse protein source at 14, with the removed solids being collected at 16. The protein extract solution 18 then is adjusted in pH at 20 to about 1.5 to about 3.4, preferably about 2.0 to about 3.0. The acid insoluble material is removed by centrifugation at 22 yielding acid insoluble solid material at 24 and an acidified protein solution at 26.

The recovered acid insoluble solid material may be optionally washed with water having the same pH as the solids, namely about 1.5 to about 3.4, preferably about 2.0 to about 3.0, at 28 and the optionally washed solids 34 may be optionally adjusted in pH to a value less than about 6.0 then dried at 48 to provide a pulse protein product designated 810PA at 50 having a protein content of at least about 60 wt % (N×6.25) d.b.

Alternatively, the optionally washed solids 34 are adjusted to a pH of generally about 6 to about 8, preferably about 6.5 to about 7.5, at 36 and dried at 38, to provide a pulse protein product designated 810PN at 40 having a protein content of at least about 60 wt % (N×6.25) d.b.

The wash centrate 30 from the optional washing step 28 may be added to the acidified protein solution 26. The solution of soluble protein may be lowered in pH within the range of about 1.5 to about 3.4, preferably about 2.0 to about 3.0 at 60. The solution of soluble protein is then subjected to concentration and optional diafiltration at 62. The retentate 64 from the concentration and optional diafiltration steps may be optionally adjusted in pH to a value less than about 6.0 then dried at 78 to provide a pulse protein product designated 810A at 80, having a protein content of at least about 60 wt % (N×6.25) d.b. Preferably, the 810A product is an isolate having a protein content of at least about 90 wt % (N×6.25) d.b. Alternatively, the retentate 64 from the concentration and optional diafiltration steps is adjusted to a pH of generally about 6 to about 8, preferably about 6.5 to about 7.5 at 66, and then dried at 68 to provide a pulse protein product designated 810N at 70, having a protein content of at least about 60 wt % (N×6.25) d.b. Preferably the 810N product is an isolate having a protein content of at least about 90 wt % (N×6.25) d.b.

The 810A and 810PA protein products may be used on their own or may be combined by dry blending at 84. Alternatively, the combined 810A/810PA product may be formed by mixing the optionally washed acid insoluble solid material, optionally adjusted to a pH of less than about 6.0 at 46 with the concentration/optional diafiltration retentate, optionally adjusted to a pH of less than about 6.0 at 76 and drying the mixture 86. The 810N and 810PN protein products may be used on their own or may be combined by dry blending at 84. Alternatively, the combined 810N/810PN product may be formed by mixing the optionally washed acid insoluble solid material, adjusted to a pH of about 6.0 to about 8.0, preferably about 6.5 to about 7.5 at 36 with the concentration/optional diafiltration retentate, adjusted to a pH of about 6.0 to about 8.0, preferably about 6.5 to about 7.5 at 66 and drying the mixture 82.

Figure 2:
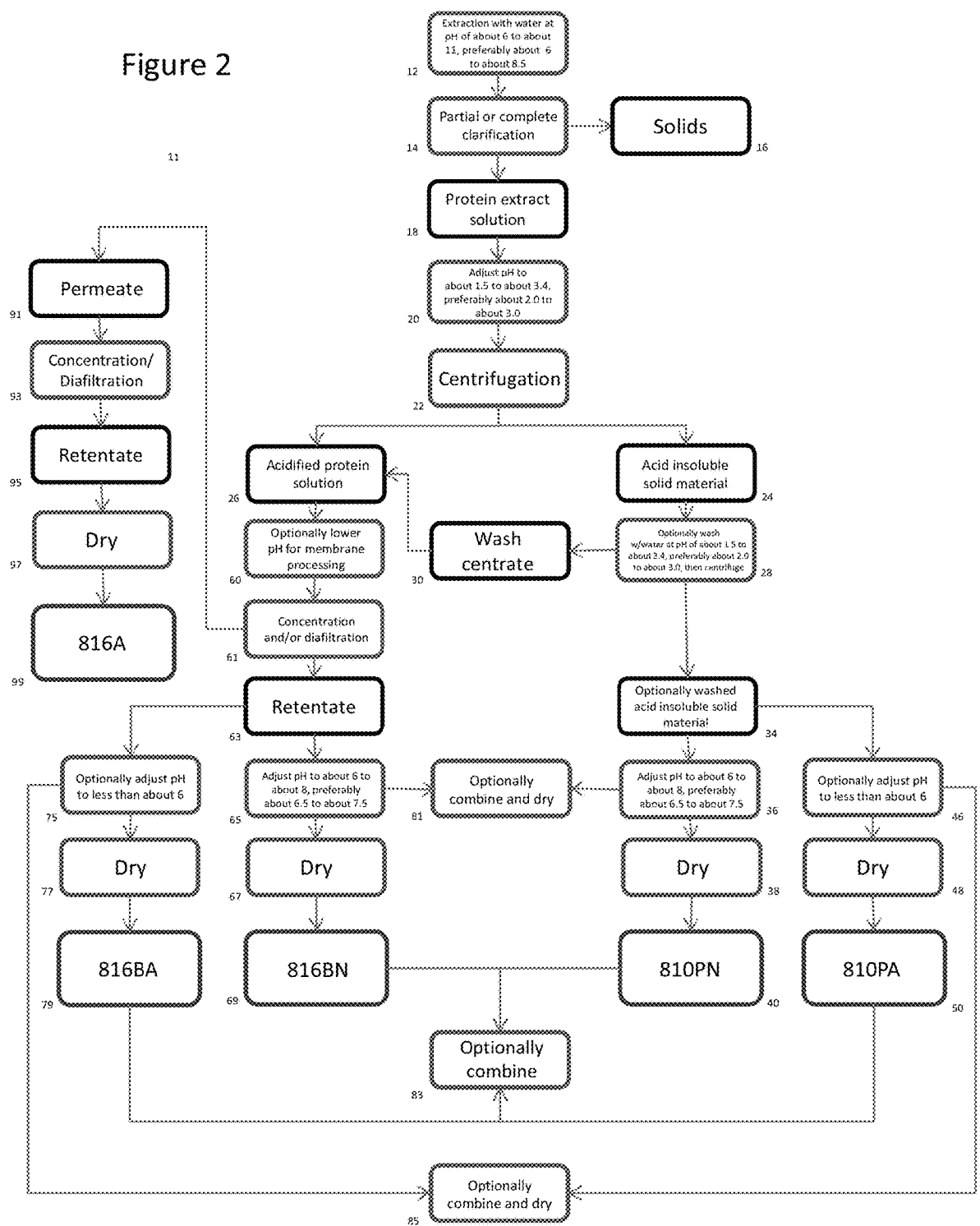
FIG. 2 is a schematic flow sheet illustrating an embodiment of the process of the present invention

Referring now to FIG. 2, which shows a process 11 according to another aspect of the present invention, a pulse protein source is subjected to an initial extraction with water at 12, at a pH of about 6 to about 11, preferably about 6.0 to about 8.5. The protein extract solution then is completely or partially clarified by the removal of residual pulse protein source at 14, with the removed solids being collected at 16. The protein extract solution 18 then is adjusted in pH at 20 to about 1.5 to about 3.4, preferably about 2.0 to about 3.0. The acid insoluble material is removed by centrifugation at 22 yielding acid insoluble solid material at 24 and an acidified protein solution at 26.

The recovered acid insoluble solid material 24 may be optionally washed with water having the same pH as the solids, namely about 1.5 to about 3.4, preferably about 2.0 to about 3.0 at 28 and the optionally washed acid insoluble solid material 34 may be optionally adjusted to a pH of less than about 6.0 at 46 then dried at 48 to provide a pulse protein product designated 810PA at 50 having a protein content of at least about 60 wt % (N×6.25) d.b.

Alternatively the optionally washed acid insoluble solid material 34 is adjusted to a pH of generally about 6.0 to about 8.0, preferably about 6.5 to about 7.5, at 36 and dried at 38, to provide a pulse protein product designated 810PN at 40 having a protein content of at least about 60 wt % (N×6.25) d.b.

The wash centrate 30 from the optional washing step may be added to the acidified protein solution 26. The solution of soluble protein may be lowered in pH within the range of about 1.5 to about 3.4, preferably about 2.0 to about 3.0 at 60. The solution of soluble protein is then subjected to microfiltration or ultrafiltration membrane processing (concentration and/or diafiltration) at 61 to separate the lower molecular weight proteins (permeate 91) from the higher molecular weight proteins (retentate 63).

The permeate from the protein fractionation step 91 is then purified by concentration and optional diafiltration using a lower pore size membrane to separate the proteins from the contaminants at 93. The retentate from the concentration and optional diafiltration steps 95 is then dried at 97 to provide a pulse protein product, having improved clarity in low pH solution, designated 816A at 99, having a protein content of at least about 60 wt % (N×6.25) d.b., preferably the product is an isolate having a protein content of at least about 90 wt % (N×6.25) d.b.

The retentate from the protein fractionation step 63 may be optionally adjusted to a pH of less than about 6.0 at 75 then dried at 77 to provide a pulse protein product designated 816BA at 79, having a protein content of at least about 60 wt % (N×6.25) d.b. Preferably, the product is an isolate having a protein content of at least about 90 wt % (N×6.25) d.b. Alternatively, the retentate from the protein fractionation step 63 may be adjusted to a pH of generally about 6 to about 8, preferably about 6.5 to about 7.5 at 65, and then dried at 67 to provide a pulse protein product designated 816BN at 69, having a protein content of at least about 60 wt % (N×6.25) d.b. Preferably, the product is an isolate having a protein content of at least about 90 wt % (N×6.25) d.b.

The 816BA and 810PA protein products may be used on their own or may be combined by dry blending at 83. Alternatively, the combined 816BA/810PA product may be formed by mixing the acid insoluble solid material that was optionally washed and optionally adjusted to a pH of less than about 6.0 46 with the protein fractionation step retentate that was optionally adjusted to a pH of less than about 6.0 75 and drying the mixture 85. The 816BN and 810PN protein products may be used on their own or may be combined by dry blending at 83. Alternatively, the combined 816BN/810PN product may be formed by mixing the pH adjusted optionally washed acid insoluble solid material adjusted to a pH of about 6.0 to about 8.0, preferably about 6.5 to about 7.5 36 with the protein fractionation step retentate adjusted to a pH of about 6.0 to about 8.0, preferably about 6.5 to about 7.5 65 and drying the mixture 81.

EXAMPLES

Example 1

This Example describes the preparation of pulse protein products according to an embodiment of the method of the present invention.

36 kg of yellow pea protein concentrate was added to 600 L of reverse osmosis purified water at ambient temperature and agitated for 10 minutes to provide an aqueous protein solution. A portion of the suspended solids were removed by centrifugation using a decanter centrifuge and 'a' kg of protein solution having a protein content of about 'b' % by weight was collected. The pH of the protein solution was then lowered to a target pH of 'c' by the addition of HCl solution (concentrated (22 BÉ) HCl diluted with an equal volume of water) and the solution centrifuged using a disc stack centrifuge to provide 'd' L of acidified protein solution, having a pH of 'e' and 'f' kg of acid insoluble solid material.

The acidified protein solution, having a protein content of 'g' wt %, was warmed then reduced in volume from 'h' L to 'i' L by concentration on a polyethersulfone membrane having a molecular weight cut-off of 'j' daltons, operated at a temperature of about 'k' ° C. The protein solution, with a protein content of 'l' wt %, was then diafiltered on the same membrane with 'm' L of RO water 'n', with the diafiltration operation conducted at about 'o'° C. The diafiltered protein solution, having a protein content of 'p' wt % was then further concentrated to a protein content of 'q' wt %. 'r' of diafiltered and concentrated protein solution was obtained and represented a yield of about 's' % of the protein in the protein solution arising from the separation step using the decanter centrifuge. 't' kg of diafiltered and concentrated protein solution was diluted with 'u' L of water adjusted to pH 2.7 with HCl solution. The diluted solution was spray dried to yield a product found to have a protein content of 'v' % (N×6.25) d.b. The product was termed 'w' YP810A. 'x' of diafiltered and concentrated protein solution was diluted with 'y' L of RO water and the pH of the sample raised to 'z' using NaOH/KOH solution. The neutralized solution was spray dried to yield a product found to have a protein content of 'aa'% (N×6.25) d.b. The product was termed 'w' YP810N.

The acid insoluble solid material collected from the disc stack centrifuge had a protein content of 'ab' wt %. A 'ac' kg portion of the acid insoluble solid material was mixed with 'ad' L of RO water 'ae' for 30 minutes at ambient temperature then centrifuged using a 'af' centrifuge. 'ag' kg of washed acid insoluble solid material was collected after the water wash step having a protein content of 'ah' wt % and represented a yield of about 'ai' % of the protein in the protein solution arising from the separation step using the decanter centrifuge. The washed acid insoluble solid material was then mixed with 'aj' L of RO water and pasteurized at about 'ak' ° C. for about 'al' minutes. 'am' kg of pasteurized, washed acid insoluble solid material was adjusted in pH to 'an' by the addition of HCl solution then spray dried to yield a product found to have a protein content of 'ao' (N×6.25) d.b. The product was termed 'w' YP810PA. 'ap' kg of pasteurized, washed acid insoluble solid material was mixed with 'aq' L of RO water then the pH was raised to 'ar' using a NaOH/KOH solution and the sample spray dried to yield a product found to have a protein content of 'as'% (N×6.25) d.b. The product was termed 'w' YP810PN. The parameters 'a' to 'as' are set forth in the following Table 1:

TABLE 1

Parameters for the runs to produce pulse 810 products

| w | YP24-C26-14A | YP26-F17-14A | YP26-F18-14A | YP26-F19-14A | YP26-F23-14A |
|---|---|---|---|---|---|
| a | 588.88 | 611.12 | 613.14 | 611.26 | 609.68 |
| b | 2.83 | 3.01 | 2.94 | 2.84 | 2.94 |
| c | 3 | 3 | 2.5 | 2 | 2 |
| d | 487 | 511 | 517 | 510 | 523 |
| e | 3.09 | 3.00 | 2.61 | 2.10 | 2.04 |
| f | 69.76 | 67.16 | 69.98 | 69.58 | 87.14 |
| g | 1.90 | 1.84 | 2.27 | 2.23 | 2.23 |
| h | 487 | 522 | 517 | 510 | 515 |
| i | 157 | 152 | 152 | 180 | 188 |
| j | 1,000 | 10,000 | 10,000 | 10,000 | 10,000 |
| k | 60 | 57 | 60 | 50 | 50 |
| l | 5.07 | 5.35 | 7.01 | 5.77 | 5.69 |
| m | 785 | 760 | 760 | 900 | 940 |
| n | N/A | N/A | N/A | N/A | adjusted to pH 2.0 |
| o | 60 | 59 | 60 | 50 | 50 |
| p | 4.77 | 5.32 | 6.65 | 5.68 | 5.39 |
| q | 8.62 | 8.62 | 9.64 | 9.92 | 9.58 |
| r | about 79 kg | about 90.7 L | 99 L | about 96 L | 103 L |
| s | 40.9 | 42.5 | 52.9 | 54.8 | 55.1 |
| t | 23.86 | N/A | N/A | N/A | 50 |
| u | 4.44 | N/A | N/A | N/A | 0 |
| v | 94.14 | N/A | N/A | N/A | 91.34 |
| x | 43.25 kg | 80.7 L | 91 L | 90 L | 53 L |
| y | 0 | 19.3 | 40 | 22 | 0 |
| z | 7.15 | 7.60 | 7.73 | 7.25 | 7.48 |
| aa | 91.25 | 90.76 | 88.65 | 89.39 | 87.59 |
| ab | 10.73 | 9.96 | 7.06 | 6.38 | 5.81 |
| ac | 0.5 | 67.16 | 69.98 | 69.58 | 87.14 |
| ad | 1.0 | 134 | 140 | 140 | 174.28 |
| ae | at about pH 3 | at pH 2.93 | at pH 2.54 | at pH 2.05 | at pH 2.12 |
| af | laboratory | disc stack | disc stack | disc stack | disc stack |
| ag | 0.07 | 38.02 | 38.24 | 38.14 | 42.22 |
| ah | 13.54 | 9.49 | 6.14 | 5.78 | 6.99 |
| ai | 0.1 | 19.6 | 13.0 | 12.7 | 16.5 |
| aj | N/A | 0 | 0 | 10 | 0 |
| ak | N/A | 65 | 66 | 66 | 64 |
| al | N/A | 15 | 15 | 15 | 45 |
| am | N/A | N/A | N/A | N/A | 22 |
| an | N/A | N/A | N/A | N/A | 1.86 |
| ao | N/A | N/A | N/A | N/A | 76.32 |
| ap | N/A | 36.5 | 20 | 47.68 | 22 |
| aq | N/A | 10 | 5 | 0 | 0 |
| ar | N/A | 7.70 | 7.43 | 7.40 | 7.40 |
| as | N/A | 79.91 | 73.71 | 74.23 | 73.66 |

N/A = not applicable

Example 2

This Example further describes the preparation of pulse protein products according to another embodiment of the method of the present invention.

'a' kg of 'b' was added to 'c' L of reverse osmosis purified water at ambient temperature and agitated for 10 minutes to provide an aqueous protein solution. A portion of the suspended solids were removed by centrifugation using a decanter centrifuge to produce 'd' kg of protein solution having a protein content of about 'e' % by weight. The pH of the protein solution was then lowered to a target pH of 'f' by the addition of HCl solution (concentrated (22 BÉ) HCl diluted with an equal volume of water) and the solution centrifuged using a disc stack centrifuge to provide 'g' L of acidified protein solution having a pH of 'h' and 'i' kg of acid insoluble solid material.

'j' kg of acid insoluble solid material was mixed with 'k' L of pH 'f' RO water and then the sample centrifuged using a 'l' centrifuge to provide 'm' L of acidified wash solution having pH 'n' as well as 'o' kg of washed acid insoluble solid material. 'p' L of acidified protein solution was combined with 'q' L of acidified wash solution and warmed to provide a membrane feed having a pH of 'r' and a protein content of 's' wt %. The membrane feed was reduced in volume from 't' L to 'u' L by concentration on a polyethersulfone membrane having a molecular weight cut-off of 'v' daltons, operated at a temperature of about 'w' ° C. The protein solution, with a protein content of 'x' wt %, was then diafiltered on the same membrane with 'y' L of RO water 'z', with the diafiltration operation conducted at about 'aa'° C.

The diafiltered protein solution, having a protein content of 'ab' wt % was then further concentrated to a protein content of 'ac' wt %. 'ad' of diafiltered and concentrated protein solution was obtained and represented a yield of about 'ae' % of the protein in the protein solution arising from the separation step using the decanter centrifuge. The diafiltered and concentrated protein solution was then diluted with 'af' L of RO water than pasteurized at about 'ag' ° C. for 'ah' seconds. 'ai' of 'aj' diafiltered and concentrated protein solution was diluted with 'ak' L of water and then spray dried to yield a product found to have a protein content of 'al' % (N×6.25) d.b. The product was termed 'am' 'an'. 'ao' of 'aj' diafiltered and concentrated protein solution was diluted with 'ap' L of RO water and the pH of the sample raised to 'aq' using 'ar' solution. The neutralized solution was spray dried to yield a product found to have a protein content of 'as'% (N×6.25) d.b. The product was termed 'am' 'at'.

The 'au' acid insoluble solid material was pasteurized at about 'av' ° C. for 'aw' seconds. 'ax' kg of 'ay' acid insoluble solid material was collected having a protein content of 'az' wt % and represented a yield of about 'ba' % of the protein in the protein solution arising from the separation step using the decanter centrifuge. 'bb' kg of 'ay' acid insoluble solid material was combined with 'bc' L of RO water and raised in pH to 'bd' using 'be' solution and the sample 'bf' dried to yield a product found to have a protein content of 'bg'% (N×6.25) d.b. The product was termed 'am' 'bh'.

The parameters 'a' to 'bh' are set forth in the following Table 2:

TABLE 2

Parameters for runs to produce pulse 810 products

| am | YP26-C16-15A | YP27-C25-15A | YP27-C30-15A | YP27-D21-15A | YP27-D22-15A | LE03-D30-15A | YP27-E06-15A | YP27-E25-15A |
|---|---|---|---|---|---|---|---|---|
| a | 36 | 36 | 36 | 36 | 36 | 18 | 36 | 72 |
| b | yellow pea protein concentrate | yellow pea protein concentrate | yellow pea protein concentrate | yellow pea protein concentrate | yellow pea protein concentrate | whole green lentil flour | yellow pea protein concentrate | yellow pea protein concentrate |
| c | 600 | 600 | 600 | 600 | 600 | 300 | 600 | 1200 |
| d | 603.12 | 611.96 | 605.58 | 607.89 | 609.61 | 311.38 | 600.42 | 1187.89 |
| e | 2.68 | 2.59 | 2.89 | 2.49 | 2.59 | 1.11 | 2.55 | 2.42 |
| f | 2 | 2 | 2 | 2 | 2 | 2 | 3 | 3 |
| g | NR | 550 | 543 | 515 | 505 | 255 | 507 | 1050 |
| h | 1.95 | 2.09 | 1.90 | 2.27 | 2.09 | 1.97 | 2.99 | 3.13 |
| i | NR | 71.26 | 67.28 | 79.7 | 74.00 | 32.44 | 69.81 | NR |
| j | N/A | 71.26 | 67.28 | 79.7 | 74.00 | 1 | 69.81 | N/A |
| k | N/A | 142 | 140 | 159.4 | 148 | 2 | 139.62 | N/A |
| l | N/A | disc stack | disc stack | disc stack | disc stack | laboratory | disc stack | N/A |
| m | N/A | 185 L | 199 L | 239 L | 191 L | 2.70 kg | 183 L | N/A |
| n | N/A | 2.26 | 2.13 | 2.01 | 2.08 | 1.98 | 2.96 | N/A |
| o | N/A | 23.58 | NR | 33.30 | 27.04 | 0.29 | 26.70 | N/A |
| p | NR | 550 | 543 | 515 | 505 | 255 | 507 | 1050 |
| q | N/A | 0 | 0 | 239 | 0 | 0 | 0 | N/A |
| r | 1.99 | 2.12 | 1.89 | 1.96 | 2.09 | 2.00 | 2.99 | 3.05 |
| s | 2.30 | 2.32 | 2.35 | 1.80 | 2.28 | 0.89 | 1.99 | 1.73 |
| t | 575 | 560 | 550 | 700 | 510 | 273 | 510 | 1025 |
| u | 211 | 210 | 200 | 200 | 185 | 31 | 200 | 300 |
| v | 10,000 | 100,000 | 100,000 | 100,000 | 100,000 | 1,000 | 100,000 | 100,000 |
| w | 51 | 51 | 52 | 50 | 51 | 50 | 52 | 51 |
| x | 4.91 | 5.55 | 5.61 | 4.99 | 5.62 | 5.56 | 4.88 | 5.57 |
| y | 2110 | 2100 | 2000 | 2000 | 1850 | 310 | 600 | 3000 |
| z | at pH 2 | at pH 2 | at pH 2 | at pH 2 | at pH 2 | at pH 2 | at pH 3 | at pH 3 |
| aa | 51 | 51 | 51 | 51 | 50 | 52 | 52 | 52 |
| ab | 4.65 | 5.70 | 5.58 | 4.88 | 5.41 | 3.80 | 4.58 | 5.02 |
| ac | 9.24 | 9.83 | 10.69 | 10.69 | 10.02 | 5.28 | 9.74 | 7.46 |
| ad | 120 L | 110 L | 90 L | 100 L | 95 L | 24.7 kg | 85 L | 165 L |
| ae | 68.6 | 68.2 | 55.0 | 70.6 | 60.3 | 37.6 | 54.1 | 42.8 |
| af | 0 | 0 | 0 | 0 | 0 | 0 | 0 | 40 |
| ag | N/A | N/A | N/A | 73 | 74 | 73 | 76 | 74 |

TABLE 2-continued

Parameters for runs to produce pulse 810 products

| am | YP26-C16-15A | YP27-C25-15A | YP27-C30-15A | YP27-D21-15A | YP27-D22-15A | LE03-D30-15A | YP27-E06-15A | YP27-E25-15A |
|---|---|---|---|---|---|---|---|---|
| ah | N/A | N/A | N/A | 16 | 16 | 16 | 16 | 16 |
| ai | 40.20 kg | 110 L | 76.57 L | N/A | N/A | 15.38 kg | N/A | N/A |
| aj | N/A | N/A | N/A | pasteurized | pasteurized | pasteurized | pasteurized | pasteurized |
| ak | 0 | 34.42 | 29.47 | N/A | N/A | 0 | N/A | N/A |
| al | 92.40 | 93.04 | 93.14 | N/A | N/A | 91.28 | N/A | N/A |
| an | YP810A | YP810A | YP810A | N/A | N/A | LE810A | N/A | N/A |
| ao | 35.70 kg | N/A | 13.43 L | 101.44 kg | 96.44 kg | 14.86 kg | 82.68 kg | 200 L |
| ap | 2.76 | N/A | 6.54 | 39.00 | 34.70 | 0 | 75.13 | 100 |
| aq | 6.90 | N/A | 7.25 | 7.06 | 7.05 | 7.11 | 7.34 | 7.60 |
| ar | NaOH/KOH | N/A | NaOH/KOH | NaOH/KOH | NaOH/KOH | NaOH/KOH | NaOH/KOH | NaOH |
| as | 88.87 | N/A | 89.03 | 89.04 | 89.13 | 85.06 | 90.27 | 89.55 |
| at | YP810N | N/A | YP810N | YP810N | YP810N | LE810N | YP810N | YP810N |
| au | N/A | washed | washed | washed | washed | washed | washed | N/A |
| av | 72 | 72 | 72 | 73 | 73 | N/A | 74 | N/A |
| aw | 60 | 16 | 60 | 16 | 16 | N/A | 16 | N/A |
| ax | 22.78 | 23.26 | 19.76 | 36.24 | 29.08 | 0.29 | 31.44 | N/A |
| ay | pasteurized | washed and pasteurized | washed and pasteurized | washed and pasteurized | washed and pasteurized | washed | washed and pasteurized | N/A |
| az | ND | 4.52 | 6.49 | 3.59 | 3.30 | 2.18 | ND | N/A |
| ba | ND | 6.6 | 7.3 | 8.6 | 6.1 | 0.3 | ND | N/A |
| bb | 22.78 kg | 23.26 kg | 19.76 kg | 36.24 kg | 29.08 kg | 0.24 kg | 31.44 kg | N/A |
| be | 7.00 | 0 | 5 | 0 | 0 | 0 | 0 | N/A |
| bd | 5.57 | about 5.5 | 5.62 | 5.43 | 5.66 | 5.42 | 5.61 | N/A |
| be | NaOH/KOH | NaOH/KOH | NaOH/KOH | NaOH/KOH | NaOH/KOH | NaOH/KOH | NaOH/KOH | N/A |
| bf | spray | spray | spray | spray | spray | freeze | spray | N/A |
| bg | 62.91 | 68.85 | 70.25 | 66.78 | 63.43 | 65.68 | 73.33 | N/A |
| bh | YP810PA | YP810PA | YP810PA | YP810PA | YP810PA | LE810PA | YP810PA | N/A |

N/A = not applicable,
ND = not determined,
NR = not recorded

Example 3

This Example further describes the preparation of pulse protein products according to another embodiment of the method of the present invention.

36 kg of yellow pea protein concentrate was added to 600 L of reverse osmosis purified water at ambient temperature and agitated for 10 minutes to provide an aqueous protein solution. A portion of the suspended solids were removed by centrifugation using a decanter centrifuge to produce 608.59 kg of protein solution having a protein content of about 2.54% by weight. The pH of the protein solution was then lowered to a target pH of 3 by the addition of HCl solution (concentrated (22 BE) HCl diluted with an equal volume of water) and the solution centrifuged using a disc stack centrifuge to provide 508 L of acidified protein solution having a pH of about 3.13 and 79.30 kg of acid insoluble solid material.

79.30 kg of acid insoluble solid material was mixed with 158.60 L of pH 3 RO water and then the sample centrifuged using a disc stack centrifuge to provide 201 L of acidified wash solution having pH of 3.00 as well as 29.98 kg of washed acid insoluble solid material.

500 L of acidified protein solution was combined with 200 L of acidified wash solution and warmed to provide a membrane feed having a pH of 3.10 and a protein content of 1.75 wt %. The membrane feed was reduced in volume from 700 L to 212 L by concentration on a polyethersulfone membrane having a molecular weight cut-off of 100,000 daltons, operated at a temperature of about 50° C. The protein solution, with a protein content of 5.34 wt %, was then diafiltered on the same membrane with 318 L of RO water at pH 3, with the diafiltration operation conducted at about 51° C. At this point 106 L of retentate was discarded to reduce the processing time. The remaining 106 L of retentate was diafiltered on the same membrane with an additional 901 L of RO water at pH 3, with the diafiltration operation conducted at about 51° C. The diafiltered protein solution, having a protein content of 5.04 wt % was then further concentrated to a protein content of 8.56 wt %. 47 kg of diafiltered and concentrated protein solution was obtained and represented a yield of about 26% of the protein in the protein solution arising from the separation step using the decanter centrifuge. The diafiltered and concentrated protein solution was then diluted with 20.5 L of RO water than pasteurized at about 73° C. for 16 seconds. To 70.44 kg of pasteurized, diafiltered and concentrated protein solution was added sufficient KOH/NaOH solution to adjust the pH to 7.02. The neutralized solution was spray dried to yield a product found to have a protein content of 90.08% (N×6.25) d.b. The product was termed YP27-E13-15A YP810N.

The washed acid insoluble solid material was pasteurized at about 72° C. for about 16 seconds. The pasteurized acid insoluble solid material collected had a protein content of 6.41 wt %. 29.98 kg of pasteurized acid insoluble solid material was combined with 3.28 L of RO water and sufficient NaOH/KOH solution to adjust the pH to 5.54. The sample was then spray dried to yield a product found to have a protein content of 75.15% (N×6.25) d.b. The product was termed YP27-E13-15A YP810PA.

Example 4

This Example further describes the preparation of pulse protein products according to another embodiment of the method of the present invention.

72 kg of yellow pea protein concentrate was added to 1200 L of reverse osmosis purified water at ambient temperature and agitated for 10 minutes to provide an aqueous protein solution. A portion of the suspended solids were removed by centrifugation using a decanter centrifuge and 1190.48 kg of protein solution having a protein content of about 2.57% by weight was collected. The pH of the protein solution was then lowered to a target pH of 3 by the addition of HCl solution (concentrated (22 BÉ) HCl diluted with an equal volume of water) and the solution centrifuged using a disc stack centrifuge to provide 1020 L of acidified protein solution, having a pH of about 3.02.

The acidified protein solution was then adjusted in pH to a target of 2 and warmed to provide a membrane feed having a pH of 2.08 and a protein content of 1.50 wt %. This solution was reduced in volume from 1040 L to 285 L by concentration on a polyethersulfone membrane having a molecular weight cut-off of 100,00 daltons, operated at a temperature of about 50° C. The protein solution, with a protein content of 5.28 wt %, was then diafiltered on the same membrane with 2850 L of RO water at pH 2, with the diafiltration operation conducted at about 51° C. The diafiltered protein solution, having a protein content of 4.99 wt % was then further concentrated to a protein content of 9.70 wt %. 133 L of diafiltered and concentrated protein solution was obtained and represented a yield of about 42.2% of the protein in the protein solution arising from the separation step using the decanter centrifuge. 133 L of diafiltered and concentrated protein solution was diluted with 40 L of RO water and then pasteurized at about 73° C. for 16 seconds. 173 L of pasteurized protein solution was then further diluted with 31.71 L of water and the pH of the sample raised to 7.05 using NaOH solution. The neutralized solution was then spray dried to yield a product found to have a protein content of 88.85% (N×6.25) d.b. The product was termed YP27-E26-15A YP810N.

Example 5

This Example illustrates production of the improved clarity acidic pulse protein product of an embodiment of the present invention.

36 kg of pea protein concentrate was combined with 600 L of reverse osmosis purified (RO) water and the mixture stirred for 10 minutes at ambient temperature. A portion of the suspended solids were removed by centrifugation using a decanter centrifuge and 'a' kg of protein solution having a protein content of about 'b' % by weight was collected. The pH of the protein solution was then lowered to a target pH of 'c' by the addition of HCl solution (concentrated (22 BÉ) HCl diluted with an equal volume of water) and the solution centrifuged using a disc stack centrifuge to provide 'd' L of acidified protein solution, having a pH of about 'e' and 'f' kg of acid insoluble solid material.

'g' L of acidified protein solution, having a protein concentration of 'h' wt %, was diluted with 'i' L RO water at pH 2, warmed to about 50° C. and then concentrated to 'j' L using a polyvinylidene fluoride (PVDF) microfiltration membrane having a pore size of 0.08 µm operated at a temperature of about 'k' ° C. Concurrent with the concentration step, the solution was diafiltered with an additional 'l' L of RO water at pH 2. 'm' L of microfiltration/diafiltration permeate, having a protein concentration of 'n' wt %, was then concentrated to 'o' kg using a PES ultrafiltration membrane having a pore size of 1,000 daltons operated at a temperature of about 'p' ° C. The concentrated protein solution had a protein content of 'q' wt %. This represented a yield of about 'r' % of the protein in the protein solution arising from the separation step using the decanter centrifuge. The concentrated protein solution was pasteurized at about 's' ° C. for 't' seconds and then 'u' kg of pasteurized, concentrated protein solution was spray dried to yield a protein product, having a protein content of 'v' % (N×6.25) d.b., termed 'w' YP816A.

The 'j' L of microfiltration retentate collected, having a protein content of 'x' wt % represented a yield of 'y' % of the protein in the protein solution arising from the separation step using the decanter centrifuge. The concentrated and diafiltered microfiltration retentate was pasteurized at about 'z' ° C. for 'aa' seconds. 'ab' kg of pasteurized microfiltration retentate was diluted with 'ac' L of RO water and adjusted to pH 'ad' with NaOH/KOH solution and then spray dried to form a protein product having a protein content of 'ae' % (N×6.25) d.b., termed 'w' YP816BN.

The parameters 'a' to 'ae' are set forth in the following Table 3.

TABLE 3

Parameters for the production of pulse 816 products

| w | YP27-D07-15A | YP27-D09-15A |
|---|---|---|
| a | 613.23 | 608.46 |
| b | 2.87 | 2.46 |
| c | 2 | 2 |
| d | 551 | 508 |
| e | 2.05 | 1.94 |
| f | NR | NR |
| g | 535 | 510 |
| h | 2.23 | 2.23 |
| i | 267.5 | 255 |
| j | 76 | 85 |
| k | 49 | 49 |
| l | 292.5 | 325 |
| m | 975 | 1000 |
| n | 0.19 | 0.33 |
| o | 36.85 | 37.68 |
| p | 47 | 47 |
| q | 4.90 | 4.91 |
| r | 10.3 | 12.4 |
| s | 73 | 72 |
| t | 16 | 16 |
| u | 39.15 | 39.80 |
| v | 89.71 | 89.86 |
| x | 10.73 | 9.24 |
| y | 46.3 | 52.4 |
| z | 74 | 72 |
| aa | 16 | 16 |
| ab | 79.90 | 88.58 |
| ac | 10 | 30.27 |
| ad | 7.14 | 7.20 |
| ae | 85.46 | 83.73 |

NR = not recorded

Example 6

This Example describes the production of pulse protein products according to the methods of the aforementioned U.S. patent application Ser. Nos. 13/103,528, 13/289,264, 13/556,357 and 13/642,003.

'a' kg of 'b' was combined with 'c' L of 'd' at 'e' and agitated for 'f' minutes. 'g' kg of a calcium chloride stock solution prepared by dissolving 'h' kg of calcium chloride pellets (95.5%) in 'i' L of RO water was then added and the mixture stirred for an additional 'j' minutes. The bulk of the residual solids were removed by centrifugation using a decanter centrifuge and then 'k' kg of a calcium chloride stock solution prepared by dissolving 'l' kg of calcium chloride pellets (95.5%) in 'm' L of RO water was added to the partially clarified protein solution. The fine residual solids were removed by a disc stack centrifuge to produce a centrate having a protein content of 'n' % by weight. 'o' L of centrate was added to 'p' L of RO water at 'q' and the pH of the sample lowered to 'r' with diluted HCl. The diluted and acidified centrate was further clarified by 's' to provide a clear acidified protein solution with a protein content of 't' % by weight.

The clear acidified protein solution was 'u' and then reduced in volume from 'v' L to 'w' L by concentration on a polyethersulfone membrane, having a molecular weight cut-off of 'x' daltons, operated at a temperature of about 'y' ° C. At this point the protein solution, with a protein content of 'z' wt %, was diafiltered with 'aa' L of RO water, with the diafiltration operation conducted at about 'ab' ° C. The diafiltered protein solution was then concentrated to 'ac' L and diafiltered with an additional 'ad' L of RO water, with the diafiltration operation conducted at approximately 'ae' ° C. The concentrated protein solution, having a protein content of 'af' wt % was further concentrated to a protein content of 'ag' wt %, then diluted with RO water to a protein content of 'ah' wt % to facilitate spray drying. The 'ai' of protein solution was recovered in a yield of 'aj' % of the centrate that was diluted and acidified. The concentrated and diafiltered protein solution was pasteurized at about 'ak' ° C. for 'al' seconds then dried to yield a product found to have a protein content of 'am' wt % (N×6.25) d.b. The product was given designation 'an'. The parameters 'a' to 'an' are set forth in the following Table 4.

TABLE 4

Parameters for the runs to produce YP701

| an | YP01-D11-11A YP701 | YP03-J05-11A YP701 | YP06-B07-12A YP701 | YP26-G21-14A YP701 | YP25-I16-14A YP701 |
|---|---|---|---|---|---|
| a | 20 | 30 | 70 | 54 | 151 |
| b | Yellow split pea flour | Yellow pea protein concentrate | Yellow split pea flour | Yellow pea protein concentrate | Yellow pea protein concentrate |
| c | 200 | 300 | 300 | 900 | 2509.1 |
| d | 0.15M $CaCl_2$ | 0.15M $CaCl_2$ | RO water | RO water | RO water |
| e | Ambient temperature | 60° C. | 30° C. | Ambient temperature | Ambient temperature |
| f | 30 | 30 | 60 | 10 | 10 |
| g | N/A | N/A | 14.53 | N/A | N/A |
| h | N/A | N/A | 4.53 | N/A | N/A |
| i | N/A | N/A | 10 | N/A | N/A |
| j | N/A | N/A | 15 | N/A | N/A |
| k | N/A | N/A | N/A | 243 | 520 |
| l | N/A | N/A | N/A | 13 | 31 |
| m | N/A | N/A | N/A | 230 | 535 |
| n | 1.53 | 3.50 | 2.86 | 1.30 | 1.12 |
| o | 180.4 | 254.9 | 220 | 1003 | 2715 |
| p | 231.1 | 346.2 | 143 | 680 | 1791 |
| q | Ambient temperature | 60° C. | Ambient temperature | Ambient temperature | Ambient temperature |
| r | 2.93 | 3.26 | 3.03 | 2.70 | 3.10 |
| s | filtration | filtration | filtration | N/A | N/A |
| t | 0.63 | 1.62 | 1.37 | 0.72 | 0.62 |
| u | N/A | N/A | warmed | warmed | warmed |
| v | 431 | 548 | 423 | 1000 | 4475 |
| w | 28 | 51 | 72 | 117 | 417 |
| x | 100,000 | 10,000 | 10,000 | 1,000 | 1,000 |
| y | 30 | 56 | 51 | 59 | 58 |
| z | 6.35 | 10.03 | 5.29 | 4.85 | 6.26 |
| aa | 252 | 510 | 144 | 234 | 834 |
| ab | 30 | 58 | 58 | 59 | 58 |
| ac | N/A | N/A | 36 | 63 | 255 |
| ad | N/A | N/A | 180 | N/A | N/A |
| ae | N/A | N/A | 58 | N/A | N/A |
| af | 7.62 | 9.85 | 9.97 | 9.86 | 10.59 |
| ag | N/A | N/A | 12.20 | N/A | N/A |
| ah | N/A | N/A | 6.45 | N/A | N/A |
| ai | 21 kg | 52.98 kg | 54.66 kg | 63 L | 255 L |
| aj | 58.0 | 58.5 | 56.1 | 47.6 | 88.8 |
| ak | N/A | N/A | N/A | 73 | 73 |
| al | N/A | N/A | N/A | 16 | 16 |
| am | 103.27 | 102.62 | 102.73 | 95.77 | 98.16 |

N/A = not applicable

Example 7

This Example describes the production of pulse protein products according to the methods of the aforementioned U.S. patent application Ser. No. 13/937,266.

'a' kg of 'b' was combined with 'c' L of 'd' at 'e' and agitated for 'f' minutes. 'g' kg of a calcium chloride pellets (95.5%) were added and the mixture stirred for an additional 'h' minutes. The bulk of the residual solids were removed by centrifugation using a decanter centrifuge and then 'i' kg of a calcium chloride stock solution prepared by dissolving 'j' kg of calcium chloride pellets (95.5%) per 'k' L of RO water was added to the partially clarified protein solution. The fine residual solids were removed by a disc stack centrifuge to produce a centrate having a protein content of 'l' % by weight. 'm' L of centrate was added to 'n' L of RO water at ambient temperature and the pH of the sample lowered to 'o' with diluted HCl. The diluted and acidified centrate was further clarified by 'p' to provide a clear acidified protein solution.

The clear acidified protein solution was warmed and then the solution, having a protein content of 'q' % by weight, was reduced in volume from 'r' L to 's' L by concentration on a polyethersulfone membrane, having a molecular weight cut-off of T daltons, operated at a temperature of about 'u' ° C. At this point the protein solution, with a protein content of 'v' wt %, was diafiltered with 'w' L of RO water, with the diafiltration operation conducted at about 'x' ° C. The diafiltered protein solution was then concentrated to 'y' L and diafiltered with an additional 'z' L of RO water, with the diafiltration operation conducted at approximately 'aa' ° C. The 'ab' of concentrated protein solution, having a protein content of 'ac' wt % was recovered in a yield of 'ad' % of the centrate that was diluted and acidified. The concentrated and diafiltered protein solution was pasteurized at about 'ae' ° C. for 'af' seconds then 'ag' kg of the 'ah' concentrated and diafiltered protein solution was diluted with 'ai' L of RO water. 'aj' of the diluted sample was adjusted in pH to 'ak' with 'al' solution. 'am' of the pH adjusted sample was then spray dried to yield a product found to have a protein content of 'an' wt % (N×6.25) d.b. The product was given designation 'ao' YP701N2. The parameters 'a' to 'ao' are set forth in the following Table 5.

Example 8

This Example illustrates the protein content of commercial yellow pea protein products Propulse (Nutri-Pea, Portage la Prairie, MB), Nutralys S85F (Roquette America, Inc., Keokuk, Iowa), Pisane C9 (Cosucra Groupe Warcoing, S.A., Belgium), Pea Protein YS 85% (The Scoular Company, Minneapolis, Minn. (manufactured by Yantai Shuangta Food Co., LTD, Jinling Town, Zhaoyuan City, Shandong Province, China), Empro E 86 (Emsland Group, Emlichheim, Germany). These protein products are among the most highly purified pea protein ingredients currently commercially available.

The protein content of the commercial samples was determined by combustion analysis using a Leco Nitrogen Determinator and the moisture content of the powders determined by an oven drying method. The protein content of the samples on a dry basis is shown in Table 6.

TABLE 5

Parameters for runs to produce YP701N2

| ao | YP03-L07-11A YP701N2 | YP07-C20-12A YP701N2 | YP27-E04-15A YP701N2 | YP27-E11-15A YP701N2 |
|---|---|---|---|---|
| a | 30 | 46.3 | 36 | 36 |
| b | yellow pea protein concentrate | yellow split pea flour | yellow pea protein concentrate | yellow pea protein concentrate |
| c | 300 | 300 | 600 | 600 |
| d | 0.15M CaCl$_2$ | RO water | RO water | RO water |
| e | ambient temperature | 30° C. | ambient temperature | ambient temperature |
| f | 30 | 30 | 10 | 10 |
| g | N/A | 4.53 | N/A | N/A |
| h | N/A | 15 | N/A | N/A |
| i | N/A | N/A | 137.50 | 142.84 |
| j | N/A | N/A | 1 | 1 |
| k | N/A | N/A | 17.2 | 17.2 |
| l | 3.47 | 1.94 | NR | NR |
| m | 262 | 264 | 650 | 664 |
| n | 317 | 185 | 432 | 431 |
| o | 3.27 | 2.99 | 2.90 | 3.13 |
| p | filtration | filtration | N/A | N/A |
| q | 1.23 | 0.95 | 0.62 | 0.68 |
| r | 583 | 470 | 1110 | 1097 |
| s | 60 | 66 | 110 | 145 |
| t | 10,000 | 10,000 | 1,000 | 1,000 |
| u | 56 | 58 | 59 | 58 |
| v | 10.14 | 4.75 | 4.91 | 4.69 |
| w | 600 | 132 | 220 | 290 |
| x | 59 | 59 | 59 | 60 |
| y | N/A | 28 | 44 | 57 |
| z | N/A | 140 | N/A | N/A |
| aa | N/A | 60 | N/A | N/A |
| ab | 58.36 kg | 27.88 kg | 44 L | 57 L |
| ac | 9.16 | 10.13 | 10.10 | 11.00 |
| ad | 58.9 | 55.1 | ND | ND |
| ae | N/A | N/A | 72 | 72 |
| af | N/A | N/A | 16 | 16 |
| ag | 18.86 | 27.88 | 45.16 | 51.36 |
| ah | N/A | N/A | pasteurized | pasteurized |
| ai | 18.92 | 27.88 | 2.64 | 24.34 |
| aj | all | a portion | all | all |
| ak | 7.00 | 6.93 | 7.75 | 7.27 |
| al | NaOH | NaOH | KOH/NaOH | KOH/NaOH |
| am | a portion | all | all | a portion |
| an | 102.02 | 98.72 | 96.91 | 96.14 |

N/A = not applicable
NR = not recorded
ND = not determined

TABLE 6

Protein content of commercial yellow pea products

| Product | % protein ((N × 6.25) d.b.) |
|---|---|
| Propulse | 82.33 |
| Nutralys S85F | 83.10 |
| Pisane C9 | 85.28 |
| Pea Protein YS 85% | 84.50 |
| Empro E 86 | 86.10 |

As may be seen from the values presented in Table 6, the protein content of the commercial products was similar to or slightly lower than the protein content of the products derived from the acidified pulse protein solution in the process of the present invention. The commercial products were generally higher in protein than the product derived from the acid insoluble solid material collected after the pH adjustment step in the current process.

Example 9

This Example illustrates the protein solubility of the pulse protein products prepared without the use of calcium salt according to aspects of the present invention as described in Examples 2 to 5, as well as certain commercial pea protein products and pulse protein products prepared with the use of calcium salt as described in Examples 6 and 7. Solubility was tested by a modified version of the procedure of Morr et al., J. Food Sci., 50: 1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. The pH was measured and corrected periodically during the 60 minutes stirring. After the 60 minutes of stirring, the samples were made up to 50 ml total volume with RO water, yielding a 1% w/v protein dispersion. The protein content of the dispersions was measured by combustion analysis using a Leco Nitrogen Determinator. Aliquots of the dispersions were then centrifuged at 7,800 g for 10 minutes, which sedimented insoluble material and yielded a supernatant. The protein content of the supernatant was measured by Leco analysis and the solubility of the product calculated as follows:

Solubility (%)=(% protein in supernatant/% protein in initial dispersion)×100

Values calculated as greater than 100% were reported as 100%.

The protein solubility of the various products at different pH values is shown in Table 7.

TABLE 7

Solubility of pulse protein products at different pH values

| sample | pH 2 | pH 3 | pH 4 | pH 5 | pH 6 | pH 7 |
|---|---|---|---|---|---|---|
| YP26-C16-15A YP810A | 93.7 | 100 | 20.9 | 14.0 | 18.1 | 28.2 |
| YP27-C25-15A YP810A | 97.7 | 92.2 | 11.6 | 8.4 | 17.0 | 36.0 |
| YP27-C30-15A YP810A | 100 | 94.6 | 26.5 | 14.4 | 26.3 | 37.0 |
| LE03-D30-15A LE810A | 100 | 100 | 24.3 | 13.2 | 29.5 | 50.5 |
| YP26-C16-15A YP810N | 39.8 | 29.5 | 23.1 | 18.7 | 21.7 | 28.8 |
| YP27-C30-15A YP810N | 42.6 | 28.7 | 20.0 | 12.6 | 22.0 | 17.1 |
| YP27-D21-15A YP810N | 40.6 | 34.7 | 21.8 | 12.9 | 24.8 | 34.0 |
| LE03-D30-15A LE810N | 40.8 | 33.3 | 23.8 | 10.7 | 24.5 | 38.1 |
| YP27-E06-15A YP810N | 61.1 | 43.9 | 23.1 | 12.0 | 21.6 | 33.7 |
| YP27-E13-15A YP810N | 74.0 | 49.5 | 28.1 | 22.3 | 32.4 | 47.6 |
| YP27-E26-15A YP810N | 52.8 | 44.6 | 28.0 | 25.0 | 27.5 | 37.7 |
| YP26-C16-15A YP810PA | 13.3 | 14.6 | 8.6 | 7.4 | 15.7 | 26.3 |
| YP27-C25-15A YP810PA | 11.8 | 6.5 | 6.5 | 4.3 | 8.7 | 16.1 |
| YP27-C30-15A YP810PA | 10.8 | 7.1 | 5.9 | 4.8 | 8.1 | 13.4 |
| YP27-D21-15A YP810PA | 14.4 | 7.3 | 13.2 | 14.9 | 24.1 | 23.0 |
| YP27-E06-15A YP810PA | 20.0 | 14.2 | 3.7 | 9.1 | 13.0 | 20.2 |
| YP27-D07-15A YP816A | 95.4 | 94.3 | 92.0 | 61.8 | 68.5 | 81.4 |
| YP27-D09-15A YP816A | 100 | 94.4 | 98.9 | 63.9 | 72.2 | 79.6 |
| YP27-D07-15A YP816BN | 28.7 | 20.8 | 16.5 | 12.5 | 18.9 | 24.1 |
| YP27-D09-15A YP816BN | 37.3 | 32.7 | 15.3 | 8.7 | 15.2 | 21.1 |
| Pisane C9 | 20.8 | 14.0 | 12.9 | 12.3 | 19.0 | 17.2 |
| Nutralys S85 | 32.5 | 20.4 | 14.3 | 11.0 | 17.4 | 22.3 |
| Propulse | 14.9 | 3.6 | 2.6 | 5.3 | 10.3 | 7.0 |
| YP01-D11-11A YP701 | 98.2 | 99.1 | 99.5 | 50.9 | 20.4 | 39.3 |
| YP03-J05-11A YP701 | 100 | 94.7 | 96.7 | 42.2 | 0.0 | 20.6 |
| YP06-B07-12A YP701 | 98.9 | 100 | 100 | ND | ND | 18.8 |
| YP03-L07-11A YP701N2 | 100 | 100 | 59.3 | 27.9 | 20.4 | 24.4 |
| YP07-C20-12A YP701N2 | 92.7 | 97.8 | 14.0 | 6.7 | 6.3 | 7.8 |

ND = not determined

As may be seen from the results shown in Table 7, the different products formed by the different aspects of the present invention have different solubility profiles. The product formed from the acidified protein solution of the present invention and dried without a neutralization step (810A) was highly soluble at pH 2 and 3 but had limited solubility at the higher pH values tested. When the product formed from the acidified protein solution of the present invention was neutralized before drying (810N), the product became less soluble at pH 2 and 3. The solubility values obtained for the 810N products were generally higher than the solubility values obtained for the commercial pea protein products across the pH range tested. The product derived from the acid insoluble solid material after the acidification step (810PN) was found to have poor protein solubility across the pH range. The improved clarity, acid soluble protein product of the present invention (816A) was highly soluble over a broader pH range (2-4) compared to the 810A. The 816A was also notably more soluble than the 810A at pH values between 5 and 7. The by-product of the preparation of the improved clarity, acid soluble product (816BN) had limited solubility across the pH range, with the solubility values somewhat between those found for the 810N and the 810PN. The 810A product of the present invention had a solubility profile different from the acidic product of the calcium salt process (701). The 810N product of the present invention had a solubility profile different from the neutralized product of the calcium salt process (701N2).

Example 10

This Example illustrates the molecular weight profile of the pulse protein products prepared without the use of calcium salt according to aspects of the present invention as described in Examples 1 to 5 as well as certain commercial pea protein products and pulse protein products prepared with the use of calcium salt as described in Examples 6 and 7.

Molecular weight profiles were determined by size exclusion chromatography using a Varian ProStar HPLC system equipped with a 300×7.8 mm Phenomenex BioSep S-2000 series column. The column contained hydrophilic bonded silica rigid support media, 5 micron diameter, with 145 Angstrom pore size.

Before the pulse protein samples were analyzed, a standard curve was prepared using a Biorad protein standard (Biorad product #151-1901) containing proteins with known molecular weights between 17,000 Daltons (myoglobulin) and 670,000 Daltons (thyroglobulin) with Vitamin B12 added as a low molecular weight marker at 1,350 Daltons. A 0.9% w/v solution of the protein standard was prepared in water, filtered with a 0.45 µm pore size filter disc then a 50 µL aliquot run on the column using a mobile phase of 0.05M phosphate/0.15M NaCl, pH 6 containing 0.02% sodium azide. The mobile phase flow rate was 1 mL/min and components were detected based on absorbance at 280 nm. Based on the retention times of these molecules of known molecular weight, a regression formula was developed relating the natural log of the molecular weight to the retention time in minutes.

Retention time (min)=−0.865×1$n$(molecular weight)+17.154($r^2$=0.98).

For the analysis of the pulse protein samples, 0.05M phosphate/0.15M NaCl, pH 6 containing 0.02% sodium azide was used as the mobile phase and also to dissolve dry samples. Protein samples were mixed with mobile phase solution to a concentration of 1% w/v, placed on a shaker for at least 1 hour then filtered using 0.45 µm pore size filter discs. Sample injection size was 50 µL. The mobile phase flow rate was 1 mL/minute and components were detected based on absorbance at 280 nm.

The above regression formula relating molecular weight and retention time was used to calculate retention times that corresponded to molecular weights of 100,000 Da, 15,000 Da, 5,000 Da and 1,000 Da. The HPLC ProStar system was used to calculate the peak areas lying within these retention time ranges and the percentage of protein ((range peak area/total protein peak area)×100) falling in a given molecular weight range was calculated. Note that the data was not corrected by protein response factor.

The molecular weight profiles of the products prepared as described in Examples 1-7 and the commercial products are shown in Table 8.

TABLE 8

HPLC protein profile of various products

| product | % >100,000 Da | % 15,000-100,000 Da | % 5,000-15,000 Da | % 1,000-5,000 Da |
|---|---|---|---|---|
| YP24-C26-14A YP810N | 12.4 | 15.5 | 17.9 | 54.2 |
| YP26-F17-14A YP810N | 14.7 | 17.5 | 23.6 | 44.2 |
| YP26-F18-14A YP810N | 12.2 | 17.8 | 22.2 | 47.9 |
| YP26-F19-14A YP810N | 14.8 | 28.2 | 23.3 | 33.7 |
| YP26-F23-14A YP810N | 17.6 | 30.4 | 26.2 | 25.8 |
| YP26-C16-15A YP810N | 9.2 | 21.8 | 19.6 | 49.4 |
| YP27-C30-15A YP810N | 11.8 | 22.9 | 20.2 | 45.0 |
| YP27-D21-15A YP810N | 10.0 | 21.7 | 20.6 | 47.7 |
| YP27-D22-15A YP810N | 10.4 | 22.0 | 19.4 | 48.2 |
| LE03-D30-15A LE810N | 17.3 | 37.2 | 22.2 | 23.3 |
| YP27-E06-15A YP810N | 10.2 | 15.8 | 20.8 | 53.1 |
| YP27-E13-15A YP810N | 13.9 | 15.5 | 17.5 | 53.0 |
| YP27-E25-15A YP810N | 13.8 | 17.7 | 18.7 | 49.9 |
| YP27-E26-15A YP810N | 11.6 | 26.3 | 16.8 | 45.3 |
| YP24-C26-14A YP810A | 13.2 | 20.8 | 24.9 | 41.0 |
| YP26-F23-14A YP810A | 18.6 | 31.7 | 35.0 | 14.8 |
| YP26-C16-15A YP810A | 17.2 | 30.3 | 31.5 | 21.0 |
| YP27-C25-15A YP810A | 13.9 | 29.5 | 27.7 | 28.9 |
| YP27-C30-15A YP810A | 15.1 | 28.6 | 31.4 | 25.0 |
| LE03-D30-15A LE810A | 25.0 | 33.1 | 22.0 | 19.9 |
| YP26-F17-14A YP810PN | 26.8 | 37.3 | 17.9 | 18.0 |
| YP26-F18-14A YP810PN | 21.6 | 41.8 | 18.5 | 18.2 |
| YP26-F19-14A YP810PN | 18.4 | 52.7 | 15.9 | 12.9 |
| YP26-F23-14A YP810PN | 33.8 | 46.1 | 10.6 | 9.4 |
| YP26-F23-14A YP810PA | 4.0 | 30.5 | 31.7 | 33.8 |
| YP26-C16-15A YP810PA | 25.5 | 49.7 | 13.8 | 11.0 |
| YP27-C25-15A YP810PA | 8.6 | 38.9 | 25.5 | 27.0 |
| YP27-C30-15A YP810PA | 34.6 | 47.1 | 10.0 | 8.3 |
| YP27-D21-15A YP810PA | 10.4 | 20.7 | 18.0 | 50.8 |
| YP27-D22-15A YP810PA | 13.2 | 39.0 | 22.2 | 25.5 |
| LE03-D30-15A LE810PA | 39.3 | 32.0 | 10.6 | 18.1 |
| YP27-E06-15A YP810PA | 12.0 | 21.0 | 23.9 | 43.1 |
| YP27-E13-15A YP810PA | 9.5 | 52.6 | 18.2 | 19.8 |
| YP27-D07-15A YP816A | 5.3 | 34.4 | 46.2 | 14.0 |
| YP27-D09-15A YP816A | 6.4 | 34.9 | 45.3 | 13.4 |
| YP27-D07-15A YP816BN | 10.5 | 24.8 | 19.1 | 45.7 |
| YP27-D09-15A YP816BN | 10.9 | 18.4 | 15.7 | 55.0 |
| YP01-D11-11A YP701 | 27.1 | 42.6 | 12.7 | 17.7 |
| YP03-J05-11A YP701 | 27.4 | 50.3 | 13.9 | 8.4 |
| YP06-B07-12A YP701 | 0.6 | 69.2 | 15.4 | 14.8 |
| YP26-G21-14A YP701 | 13.0 | 36.7 | 38.4 | 11.9 |
| YP25-I16-14A YP701 | 14.9 | 42.6 | 30.3 | 12.2 |
| YP03-L07-11A YP701N2 | 19.7 | 52.7 | 15.9 | 11.8 |
| YP07-C20-12A YP701N2 | 12.1 | 46.8 | 20.3 | 20.8 |

TABLE 8-continued

HPLC protein profile of various products

| product | % >100,000 Da | % 15,000-100,000 Da | % 5,000-15,000 Da | % 1,000-5,000 Da |
|---|---|---|---|---|
| YP27-E04-15A YP701N2 | 15.8 | 40.4 | 30.2 | 13.6 |
| YP27-E11-15A YP701N2 | 18.6 | 39.8 | 27.9 | 13.8 |
| Pisane C9 | 14.6 | 57.9 | 16.7 | 10.7 |
| Scoular Pea Protein 85YS | 6.2 | 39.3 | 28.0 | 26.6 |
| Empro E 86 | 17.3 | 42.2 | 16.2 | 24.3 |

As may be seen from the results presented in Table 8, the pulse protein products derived from the acidified protein solutions of the present invention (810A, 810N, 816A, and 816BN) had protein profiles that were different from the commercial pea protein products and the products prepared by processing with calcium salt.

Example 11

This Example contains an evaluation of the phytic acid content of the pulse products prepared according to aspects of the present invention as described in Examples 1 to 5 as well as certain commercial pea protein products and pulse protein products prepared with the use of calcium salt as described in Examples 6 and 7. Phytic acid content was determined using the method of Latta and Eskin (J. Agric. Food Chem., 28: 1313-1315).

The results obtained are set forth in the following Table 9.

TABLE 9

Phytic acid content of various products

| sample | wt % phytic acid d.b. |
|---|---|
| YP24-C26-14A YP810N | 2.15 |
| YP26-F17-14A YP810N | 2.83 |
| YP26-F18-14A YP810N | 2.34 |
| YP26-F19-14A YP810N | 2.73 |
| YP26-F23-14A YP810N | 2.51 |
| YP26-C16-15A YP810N | 3.40 |
| YP27-C30-15A YP810N | 3.12 |
| YP27-D21-15A YP810N | 3.15 |
| YP27-D22-15A YP810N | 3.02 |
| LE03-D30-15A LE810N | 3.99 |
| YP27-E06-15A YP810N | 2.99 |
| YP27-E13-15A YP810N | 2.78 |
| YP27-E25-15A YP810N | 2.45 |
| YP27-E26-15A YP810N | 2.56 |
| YP24-C26-14A YP810A | 2.32 |
| YP26-F23-14A YP810A | 2.99 |
| YP26-C16-15A YP810A | 4.12 |
| YP27-C25-15A YP810A | 3.48 |
| YP27-C30-15A YP810A | 3.79 |
| LE03-D30-15A LE810A | 3.66 |
| YP26-F17-14A YP810PN | 3.66 |
| YP26-F18-14A YP810PN | 3.73 |
| YP26-F19-14A YP810PN | 3.71 |
| YP26-F23-14A YP810PN | 3.96 |
| YP26-F23-14A YP810PA | 4.41 |
| YP26-C16-15A YP810PA | 3.26 |
| YP27-C25-15A YP810PA | 3.50 |
| YP27-C30-15A YP810PA | 4.16 |
| YP27-D21-15A YP810PA | 3.52 |
| YP27-D22-15A YP810PA | 3.51 |
| LE03-D30-15A YP810PA | 3.99 |
| YP27-E06-15A YP810PA | 3.22 |
| YP27-E13-15A YP810PA | 3.31 |
| YP27-D07-15A YP816A | 0.46 |
| YP27-D09-15A YP816A | 0.49 |
| YP27-D07-15AY P816BN | 3.88 |
| YP27-D09-15AY P816BN | 3.04 |
| YP01-D11-11A YP701 | 0.27 |

TABLE 9-continued

Phytic acid content of various products

| sample | wt % phytic acid d.b. |
|---|---|
| YP03-J05-11A YP701 | 0.15 |
| YP06-B07-12A YP701 | 0.02 |
| YP26-G21-14A YP701 | 0.58 |
| YP03-L07-11A YP701N2 | 0.07 |
| YP07-C20-12A YP701N2 | 0.00 |
| Pisane C9 | 1.94 |
| Nutralys S85F | 2.24 |
| Propulse | 2.72 |

As may be seen from the results presented in Table 9, the phytic acid content of all of the products of aspects of the present invention were higher in phytic acid than the products prepared with calcium salt, with the exception of the acid soluble product having improved clarity (816A). Product derived from the acidified protein solutions of the present invention had phytic acid contents comparable to the commercial products tested. The phytic acid content of the product derived from the acid insoluble solid material according to an aspect of the present invention appeared to be higher in phytic acid compared to the commercial products tested.

Example 12

This Example contains an evaluation of the acid hydrolysable carbohydrate content of the pulse products prepared according to aspects of the present invention as described in Examples 1 to 5 as well as certain commercial pea protein products and pulse protein products prepared with the use of calcium salt as described in Examples 6 and 7. The acid hydrolysable carbohydrate content was determined according to the method of Dubois et al. (Anal. Chem., 28: 350-356). The results are shown in the following Table 10.

TABLE 10

Acid hydrolysable carbohydrate content of samples

| sample | % acid hydrolysable carbohydrates d.b. |
|---|---|
| YP24-C26-14A YP810N | 2.29 |
| YP26-F17-14A YP810N | 2.09 |
| YP26-F18-14A YP810N | 2.24 |
| YP26-F19-14A YP810N | 1.93 |
| YP26-F23-14A YP810N | 1.85 |
| YP26-C16-15A YP810N | 2.04 |
| YP27-C30-15A YP810N | 1.76 |
| YP27-D21-15A YP810N | 2.24 |
| YP27-D22-15A YP810N | 1.73 |
| LE03-D30-15A LE810N | 2.66 |
| YP27-E06-15A YP810N | 2.79 |
| YP27-E13-15A YP810N | 1.95 |
| YP27-E25-15A YP810N | 5.94 |
| YP27-E26-15A YP810N | 2.18 |

TABLE 10-continued

Acid hydrolysable carbohydrate content of samples

| sample | % acid hydrolysable carbohydrates d.b. |
|---|---|
| YP24-C26-14A YP810A | 2.29 |
| YP26-F23-14A YP810A | 1.78 |
| YP26-C16-15A YP810A | 2.21 |
| YP27-C25-15A YP810A | 1.91 |
| YP27-C30-15A YP810A | 1.79 |
| LE03-D30-15A LE810A | 2.66 |
| YP26-F17-14A YP810PN | 6.43 |
| YP26-F18-14A YP810PN | 10.51 |
| YP26-F19-14A YP810PN | 9.08 |
| YP26-F23-14A YP810PN | 9.27 |
| YP26-F23-14A YP810PA | 10.75 |
| YP26-C16-15A YP810PA | 13.69 |
| YP27-C25-15A YP810PA | 16.69 |
| YP27-C30-15A YP810PA | 15.77 |
| YP27-D21-15A YP810PA | 18.40 |
| YP27-D22-15A YP810PA | 14.06 |
| YP27-E06-15A YP810PA | 10.57 |
| YP27-E13-15A YP810PA | 9.06 |
| YP27-D07-15A YP816A | 8.54 |
| YP27-D09-15A YP816A | 8.45 |
| YP27-D07-15A YP816BN | 3.13 |
| YP27-D09-15A YP816BN | 3.08 |
| YP01-D11-11A YP701 | 1.89 |
| YP03-J05-11A YP701 | 2.06 |
| YP06-B07-12A YP701 | 0.96 |
| YP26-G21-14A YP701 | 2.46 |
| YP03-L07-11A YP701N2 | 1.07 |
| YP07-C20-12A YP701N2 | 1.04 |
| Pisane C9 | 2.60 |
| Nutralys S85F | 5.74 |
| Propulse | 5.06 |

As may be seen from the results presented in Table 10, the product of the present invention derived from the acid insoluble solid material was generally higher in acid hydrolysable carbohydrate content compared to the other samples evaluated.

Example 13

This Example contains an evaluation of the colour in solution and the haze level of solutions of the pulse products prepared according to aspects of the present invention as described in Examples 1 to 5 as well as certain commercial pea protein products and pulse protein products prepared with the use of calcium salt as described in Examples 6 and 7. Solutions of the protein products were prepared by dissolving sufficient protein powder to supply 0.48 g of protein in 15 ml of RO water. The pH of the solutions was measured with a pH meter and the colour and haze level assessed using a HunterLab ColorQuest XE instrument operated in transmission mode. The results are shown in the following Table 11.

TABLE 11

Colour and haze values for samples in solution

| product | pH | L* | a* | b* | % haze |
|---|---|---|---|---|---|
| YP24-C26-14A YP810N | 6.97 | 56.08 | 3.14 | 34.50 | 97.5 |
| YP26-F17-14A YP810N | 7.50 | 56.44 | 3.10 | 29.81 | 96.1 |
| YP26-F18-14A YP810N | 7.73 | 56.12 | 2.66 | 30.14 | 96.4 |
| YP26-F19-14A YP810N | 7.40 | 59.08 | 1.86 | 30.40 | 96.6 |
| YP26-F23-14A YP810N | 7.02 | 56.59 | 1.68 | 27.57 | 98.8 |
| YP26-C16-15A YP810N | 6.31 | 56.84 | 1.66 | 26.87 | 94.7 |
| YP27-C30-15A YP810N | 6.48 | 59.24 | 1.00 | 23.77 | 95.4 |
| YP27-D21-15A YP810N | 6.88 | 59.08 | 1.92 | 28.92 | 97.4 |
| YP27-D22-15A YP810N | 7.08 | 60.26 | 1.69 | 25.39 | 97.2 |
| LE03-D30-15A LE810N | 6.49 | 38.05 | 7.62 | 26.90 | 97.6 |
| YP27-E06-15A YP810N | 7.48 | 58.64 | 3.23 | 32.00 | 97.8 |
| YP27-E13-15A YP810N | 7.05 | 58.39 | 3.83 | 31.62 | 98.1 |
| YP27-E25-15A YP810N | 7.38 | 57.32 | 3.54 | 29.39 | 97.2 |
| YP27-E26-15A YP810N | 7.10 | 60.92 | 2.24 | 25.67 | 97.1 |
| YP24-C26-14A YP810A | 3.62 | 47.55 | 5.28 | 38.05 | 97.4 |
| YP26-F23-14A YP810A | 2.62 | 61.45 | 3.40 | 25.71 | 96.9 |
| YP26-C16-15A YP810A | 2.37 | 58.65 | 2.56 | 24.59 | 94.9 |
| YP27-C25-15A YP810A | 2.57 | 57.47 | 2.72 | 24.60 | 94.7 |
| YP27-C30-15A YP810A | 2.61 | 61.72 | 2.74 | 23.51 | 94.2 |
| LE03-D30-15A LE810A | 2.55 | 59.24 | 8.11 | 39.09 | 92.7 |
| YP26-F17-14A YP810PN | 7.72 | 47.43 | 5.47 | 37.03 | 96.8 |
| YP26-F18-14A YP810PN | 7.59 | 43.58 | 7.19 | 41.13 | 96.3 |
| YP26-F19-14A YP810PN | 7.20 | 44.08 | 7.82 | 43.66 | 97.0 |
| YP26-F23-14A YP810PN | 6.23 | 37.05 | 9.89 | 42.89 | 98.6 |
| YP26-F23-14A YP810PA | 2.13 | 24.10 | 15.20 | 37.10 | 99.0 |
| YP26-C16-15A YP810PA | 5.42 | 25.71 | 18.07 | 42.59 | 95.5 |
| YP27-C25-15A YP810PA | 5.37 | 28.54 | 14.97 | 45.04 | 94.7 |
| YP27-C30-15A YP810PA | 5.67 | 28.68 | 15.39 | 44.48 | 95.2 |
| YP27-D21-15A YP810PA | 5.40 | 25.27 | 16.13 | 41.42 | 97.7 |
| YP27-D22-15A YP810PA | 5.69 | 23.97 | 16.63 | 39.60 | 97.2 |
| YP27-E06-15A YP810PA | 5.66 | 34.68 | 12.55 | 48.77 | 97.3 |
| YP27-E13-15A YP810PA | 5.62 | 33.15 | 13.72 | 48.25 | 97.7 |
| YP27-D07-15A YP816A | 2.75 | 94.11 | −0.01 | 13.15 | 20.2 |
| YP27-D09-15A YP816A | 2.63 | 95.46 | −0.23 | 12.16 | 19.9 |
| YP27-D07-15A YP816BN | 7.40 | 58.54 | 2.97 | 36.22 | 97.7 |
| YP27-D09-15A YP816BN | 7.33 | 60.43 | 2.38 | 33.98 | 98.2 |
| YP01-D11-11A YP701 | 3.45 | 93.97 | 0.54 | 12.70 | 5.0 |
| YP03-J05-11A YP701 | 3.62 | 93.64 | 0.52 | 10.97 | 6.0 |
| YP06-B07-12A YP701 | 3.43 | 96.42 | −0.35 | 9.32 | 2.1 |
| YP26-G21-14A YP701 | 3.15 | 93.87 | 0.69 | 13.12 | 28.5 |
| YP25-I16-14A YP701 | 3.19 | 92.82 | 0.99 | 14.24 | 30.7 |
| YP03-L07-11A YP701N2 | 6.63 | 49.78 | 2.48 | 24.03 | 94.9 |
| YP07-C20-12A YP701N2 | 6.56 | 46.63 | 3.63 | 26.81 | 95.7 |
| YP27-E04-15A YP701N2 | 7.86 | 51.79 | 2.74 | 25.79 | 97.2 |
| YP27-E11-15A YP701N2 | 7.37 | 50.46 | 3.32 | 26.49 | 98.1 |
| Pisane C9 | 7.68 | 45.04 | 8.57 | 47.57 | 98.8 |
| Nutralys S85F | 7.32 | 53.48 | 6.20 | 34.01 | 97.5 |
| Propulse | 6.15 | 35.33 | 12.61 | 48.79 | 96.6 |

As may be seen from the results in Table 11, the haze level of solutions of the 816A product was much lower than the haze level of solutions of the other products of the present invention, and was comparable to the haze levels of solutions of the low pH product prepared using calcium salt (701).

Example 14

This Example contains an evaluation of the dry colour of the pulse products prepared according to aspects of the present invention as described in Examples 1 to 5 as well as certain commercial pea protein products and pulse protein products prepared with the use of calcium salt as described in Examples 6 and 7. Dry colour was assessed using a HunterLab ColorQuest XE operated in reflectance mode. The results are shown in the following Table 12.

TABLE 12

Dry colour of protein products

| Product | L* | a* | b* |
|---|---|---|---|
| YP24-C26-14A YP810N | 85.03 | 0.82 | 15.53 |
| YP26-F17-14A YP810N | 84.56 | 0.55 | 12.53 |
| YP26-F18-14A YP810N | 95.61 | 1.57 | 11.46 |
| YP26-F19-14A YP810N | 95.49 | 1.74 | 13.73 |
| YP26-F23-14A YP810N | 84.06 | 0.86 | 15.65 |
| YP26-C16-15A YP810N | 84.29 | 1.24 | 14.47 |

TABLE 12-continued

Dry colour of protein products

| Product | L* | a* | b* |
|---|---|---|---|
| YP27-C30-15A YP810N | 85.47 | 0.85 | 13.16 |
| YP27-D21-15A YP810N | 84.88 | 1.01 | 15.19 |
| YP27-D22-15A YP810N | 85.37 | 0.97 | 13.46 |
| LE03-D30-15A LE810N | 76.07 | 2.01 | 7.94 |
| YP27-E06-15A YP810N | 84.77 | 0.85 | 13.08 |
| YP27-E13-15A YP810N | 84.14 | 1.36 | 14.12 |
| YP27-E25-15A YP810N | 84.38 | 0.86 | 11.67 |
| YP27-E26-15A YP810N | 85.06 | 0.94 | 12.66 |
| YP24-C26-14A YP810A | 85.06 | 1.38 | 15.35 |
| YP26-F23-14A YP810A | 85.31 | 1.35 | 14.18 |
| YP26-C16-15A YP810A | 84.87 | 0.80 | 12.16 |
| YP27-C25-15A YP810A | 86.00 | 1.16 | 12.35 |
| YP27-C30-15A YP810A | 85.61 | 1.16 | 13.05 |
| LE03-D30-15A LE810A | 81.89 | 1.77 | 12.15 |
| YP26-F17-14A YP810PN | 82.34 | 1.76 | 15.17 |
| YP26-F18-14A YP810PN | 93.22 | 2.36 | 13.47 |
| YP26-F19-14A YP810PN | 92.96 | 2.64 | 15.08 |
| YP26-F23-14A YP810PN | 82.09 | 1.97 | 16.80 |
| YP26-F23-14A YP810PA | 81.52 | 1.99 | 13.75 |
| YP26-C16-15A YP810PA | 78.00 | 3.26 | 24.10 |
| YP27-C25-15A YP810PA | 80.32 | 1.92 | 19.10 |
| YP27-C30-15A YP810PA | 79.53 | 2.70 | 19.07 |
| YP27-D21-15A YP810PA | 80.05 | 1.89 | 18.86 |
| YP27-D22-15A YP810PA | 79.94 | 1.93 | 18.40 |
| YP27-E06-15A YP810PA | 80.58 | 2.32 | 18.15 |
| YP27-E13-15A YP810PA | 80.15 | 2.45 | 17.57 |
| YP27-D07-15A YP816A | 86.49 | 0.85 | 10.17 |
| YP27-D09-15A YP816A | 97.01 | 2.05 | 8.84 |
| YP27-D07-15A YP816BN | 81.98 | 1.71 | 19.73 |
| YP27-D09-15A YP816BN | 94.09 | 2.17 | 15.69 |
| YP01-D11-11A YP701 | 86.27 | 2.21 | 9.73 |
| YP03-J05-11A YP701 | 86.79 | 1.21 | 8.74 |
| YP06-B07-12A YP701 | 87.54 | 0.62 | 8.60 |
| YP26-G21-14A YP701 | 84.10 | 1.98 | 11.02 |
| YP25-I16-14A YP701 | 82.63 | 2.34 | 12.16 |
| YP03-L07-11A YP701N2 | 84.98 | 0.35 | 9.89 |
| YP07-C20-12A YP701N2 | 87.58 | 0.64 | 8.66 |
| YP27-E04-15A YP701N2 | 83.53 | 0.54 | 11.21 |
| YP27-E11-15A YP701N2 | 82.63 | 0.65 | 10.79 |
| Nutralys S85F | 79.21 | 5.23 | 20.22 |
| Pisane C9 | 81.31 | 2.96 | 19.46 |
| Scoular Pea Protein 85YS | 74.07 | 4.28 | 22.72 |
| Empro E 86 | 77.25 | 4.58 | 22.84 |

As may be seen from the results in Table 12, the colour of the products of the present invention were similar to the colour of the products prepared with calcium salt (701 and 701N2) and generally lighter, less red and less yellow than the commercial products.

Example 15

This Example illustrates a comparison of the flavour of YP26-F17-14A YP810N, prepared as described in Example 1 with that of the commercial yellow pea protein product Pisane C9.

Samples were prepared for sensory evaluation by dissolving sufficient protein powder to supply 5 g of protein in 250 ml purified drinking water. The pH of the solution of YP810N was determined to be 7.13 while the pH of the solution of Pisane C9 was 7.56. Food grade HCl was added to both solutions to adjust the pH to 7. An informal panel of seven panelists was asked to blindly compare the samples and indicate which sample had less vegetable flavour.

Seven out of seven panelists indicated that the YP810N had less vegetable flavour.

Example 16

This Example illustrates a comparison of the flavour of YP27-C30-15A YP810N, prepared as described in Example 2 with that of the commercial yellow pea protein product Pisane C9.

Samples were prepared for sensory evaluation by dissolving sufficient protein powder to supply 5 g of protein in 250 ml purified drinking water. The pH of the solution of YP810N was determined to be 6.56 while the pH of the solution of Pisane C9 was 7.92. Food grade NaOH was added to the solution of YP810N to raise the pH to 6.99. Food grade HCl was added to the solution of Pisane C9 to lower the pH to 6.97. An informal panel of 9 panelists was asked to blindly compare the samples and indicate which sample had less vegetable flavour.

8 out of 9 panelists indicated that the YP810N had less vegetable flavour, while 1 panelist could not distinguish which sample had less vegetable flavour.

Example 17

This Example illustrates a comparison of the flavour of YP27-C30-15A YP810N, prepared as described in Example 2 with that of the commercial yellow pea protein product Pea Protein YS 85%.

Samples were prepared for sensory evaluation by dissolving sufficient protein powder to supply 5 g of protein in 250 ml purified drinking water. The pH of the solution of YP810N was determined to be 6.65 while the pH of the solution of Pea Protein YS 85% was 7.16. Food grade NaOH was added to the solution of YP810N to raise the pH to 7.00. Food grade HCl was added to the solution of Pea Protein YS 85% to lower the pH to 7.00. An informal panel of 10 panelists was asked to blindly compare the samples and indicate which sample had less vegetable flavour.

8 out of 10 panelists indicated that the YP810N had less vegetable flavour. One panelist indicated that the Pea Protein YS 85% had less vegetable flavour and one panelist could not identify which sample had less vegetable flavour.

Example 18

This Example illustrates a comparison of the flavour of YP27-E06-15A YP810N, prepared as described in Example 2 with that of the commercial yellow pea protein product Pea Protein YS 85%.

Samples were prepared for sensory evaluation by dissolving sufficient protein powder to supply 5 g of protein in 250 ml purified drinking water. The pH of the solution of YP810N was determined to be 7.49 and the pH of the solution of Pea Protein YS 85% was 7.10. Food grade HCl was added to the solution of YP810N to lower the pH to 7.03. An informal panel of 9 panelists was asked to blindly compare the samples and indicate which sample had less vegetable flavour.

6 out of 9 panelists indicated that the YP810N had less vegetable flavour. Two panelists indicated that the Pea Protein YS 85% had less vegetable flavour, while one panelist could not distinguish which sample had less vegetable flavour.

Example 19

This Example illustrates a comparison of the flavour of YP27-C30-15A YP810A, prepared as described in Example 2 with that of the commercial yellow pea protein product Pisane C9.

Samples were prepared for sensory evaluation by dissolving sufficient protein powder to supply 5 g of protein in 250 ml purified drinking water. The pH of the solution of YP810A was determined to be 2.77 while the pH of the solution of Pisane C9 was 7.90. Food grade NaOH was added to the solution of YP810A to raise the pH to 3.00. Food grade HCl was added to the solution of Pisane C9 to lower the pH to 3.00. An informal panel of 9 panelists was asked to blindly compare the samples and indicate which sample had less vegetable flavour.

8 out of 9 panelists indicated that the YP810A had less vegetable flavour. One panelist indicated that the Pisane C9 had less vegetable flavour.

Example 20

This Example illustrates a comparison of the flavour of YP27-C30-15A YP810A, prepared as described in Example 2 with that of the commercial yellow pea protein product Pea Protein YS 85%.

Samples were prepared for sensory evaluation by dissolving sufficient protein powder to supply 5 g of protein in 250 ml purified drinking water. The pH of the solution of YP810A was determined to be 2.82 while the pH of the solution of Pea Protein YS 85% was 7.25. Food grade NaOH was added to the solution of YP810A to raise the pH to 3.00. Food grade HCl was added to the solution of Pea Protein YS 85% to lower the pH to 3.00. An informal panel of 9 panelists was asked to blindly compare the samples and indicate which sample had less vegetable flavour.

8 out of 9 panelists indicated that the YP810A had less vegetable flavour. One panelist could not distinguish which sample had less vegetable flavour.

SUMMARY OF THE DISCLOSURE

In summary of this disclosure, there is provided novel and inventive methods of producing pulse protein products which methods do not involve the use of salts for extraction of the protein from protein source. There is also provided novel and inventive pulse protein products which pulse protein products have enhanced taste. Modifications are possible within the scope of this invention.

What we claim is:

1. A pulse protein product having (a) a protein content of greater than 90 wt % (N×6.25) d.b., and which has a phytic acid content of greater than 2 wt % d.b. and which has an a* reading for a dried powder of the pulse protein product of less than 2.5 and a b* reading for the dried powder of less than 17 and which is produced by a process which comprises: (a) extracting a pulse protein source with water at a pH of about 6 to about 11 to cause solubilization of pulse protein from the protein source and to form an aqueous pulse protein solution, (b) at least partially separating the aqueous pulse protein solution from residual pulse protein source, (c) adjusting the pH of the aqueous pulse protein solution to a pH of about 1.5 to about 3.4 to produce an acidified pulse protein solution, (d) separating the acid insoluble solid material from the acidified pulse protein solution, (e) concentrating the acidified pulse protein solution by a selective membrane technique, (f) diafiltering the concentrated pulse protein solution, and (g) drying the concentrated and diafiltered pulse protein solution.

2. The pulse protein product according to claim 1 which is a yellow pea protein product.

3. The pulse protein product according to claim 1 which is a green lentil protein product.

4. The pulse protein product according to claim 1, wherein the pH of the concentrated and diafiltered acidified pulse protein solution is adjusted to a value selected from the group consisting of less than about 8.0, about 6.0 to about 8.0 and about 6.5 to about 7.5, prior to drying step (g).

* * * * *